(12) United States Patent
Melnichuk et al.

(10) Patent No.: US 8,088,832 B2
(45) Date of Patent: Jan. 3, 2012

(54) SYSTEM AND METHOD FOR CONVERTING BIOMASS TO ETHANOL VIA SYNGAS

(75) Inventors: Larry Jack Melnichuk, Burlington (CA); Karen Venita Kelly, Burlington (CA); Robert S. Davis, Boston, MA (US)

(73) Assignee: Woodland Biofuels Inc., Mississauga, Ontario (CA)

( * ) Notice: Subject to any disclaimer, the term of this patent is extended or adjusted under 35 U.S.C. 154(b) by 1243 days.

(21) Appl. No.: 11/784,508

(22) Filed: Apr. 5, 2007

(65) Prior Publication Data

US 2007/0270511 A1  Nov. 22, 2007

Related U.S. Application Data

(60) Provisional application No. 60/789,067, filed on Apr. 5, 2006, provisional application No. 60/881,189, filed on Jan. 19, 2007.

(51) Int. Cl.
*C07C 27/00* (2006.01)
*C07C 27/04* (2006.01)
*C07C 51/12* (2006.01)
*C07C 67/36* (2006.01)

(52) U.S. Cl. ........ 518/700; 518/702; 518/703; 518/704; 568/885; 562/519; 560/232

(58) Field of Classification Search .......... 518/700, 518/702–704; 568/885; 562/519; 560/232
See application file for complete search history.

(56) References Cited

U.S. PATENT DOCUMENTS

| | | | |
|---|---|---|---|
| 3,972,952 A | 8/1976 | Clark | 260/642 R |
| 4,357,480 A | 11/1982 | Barlow | 568/902 |
| 4,395,495 A | 7/1983 | Cummings | 518/704 |
| 4,454,358 A | 6/1984 | Kummer et al. | 568/885 |
| 4,498,909 A | 2/1985 | Milner | 48/209 |
| 4,747,355 A | 5/1988 | van Berkum | 110/229 |
| 4,766,154 A | 8/1988 | Bonnell | 518/700 |
| 4,823,740 A | 4/1989 | Ohshita | 122/4 D |
| 4,848,249 A | 7/1989 | LePori | 112/234 |
| 4,929,254 A | 5/1990 | Kooiman | 48/76 |
| 4,954,665 A | 9/1990 | Vidal | 568/902.2 |
| 4,971,599 A | 11/1990 | Cordell | 48/76 |
| 5,059,404 A | 10/1991 | Mansour | 423/201 |
| 5,079,267 A | 1/1992 | Kao | 518/704 |
| 5,120,885 A | 6/1992 | Tsukada | 568/885 |
| 5,138,982 A | 8/1992 | Ohshita | 122/4 D |
| 5,189,203 A | 2/1993 | Hansen | 560/232 |
| 5,218,931 A | 6/1993 | Gorzegno | 122/4 D |
| 5,226,927 A | 7/1993 | Rundstrom | 48/76 |
| 5,233,099 A | 8/1993 | Tabata | 568/885 |
| 5,233,100 A | 8/1993 | Tabata | 568/885 |
| 5,269,262 A | 12/1993 | Salonen | 122/4 D |
| 5,279,234 A | 1/1994 | Bender | 110/210 |
| 5,286,900 A | 2/1994 | Hansen | 560/232 |
| 5,290,327 A | 3/1994 | Rossle | 48/111 |
| 5,334,755 A | 8/1994 | Yoneda | 562/519 |
| 5,344,848 A | 9/1994 | Steinberg | 518/704 |
| 5,414,161 A | 5/1995 | Uhm | 568/885 |
| 5,430,178 A | 7/1995 | Uhm | 560/232 |
| 5,488,143 A | 1/1996 | Uhm | 560/232 |
| 5,573,559 A | 11/1996 | Hilliard | 48/203 |
| 5,580,362 A | 12/1996 | Manulescu | 48/197 R |
| 5,589,599 A | 12/1996 | McMullen | 585/240 |
| 5,599,976 A | 2/1997 | Scates | 562/519 |
| 5,607,487 A | 3/1997 | Taylor | 48/111 |
| 5,620,488 A | 4/1997 | Hirayama | 48/197 R |
| 5,625,094 A | 4/1997 | Nobel | 560/232 |
| 5,663,430 A | 9/1997 | Morris | 562/608 |
| 5,666,890 A | 9/1997 | Craig | 110/229 |
| 5,695,532 A | 12/1997 | Johnson | 48/203 |
| 5,696,284 A | 12/1997 | Baker | 560/232 |
| 5,723,660 A | 3/1998 | Morimoto | 562/519 |
| 5,728,871 A | 3/1998 | Joensen | 562/519 |
| 5,750,007 A | 5/1998 | Clode | 203/3 |
| 5,773,642 A | 6/1998 | Denis | 560/232 |
| 5,840,969 A | 11/1998 | Joensen | 562/519 |
| 5,874,610 A | 2/1999 | Clode | 560/232 |
| 5,877,348 A | 3/1999 | Ditzel | 562/519 |
| 5,883,289 A | 3/1999 | Denis | 560/232 |
| 5,883,295 A | 3/1999 | Sunley | 562/519 |
| 5,900,224 A | 5/1999 | Fujimura | 423/359 |

(Continued)

FOREIGN PATENT DOCUMENTS

CA    2362687    8/2000
(Continued)

OTHER PUBLICATIONS

David C. Dayton, R&D Needs for Integrated Biorefineries. The 30 x 30 Vision (30% of 2004 Motor Gasoline Supplied by Biofuels by 2030);Thermochemical Area Leader, National Renewable Energy Laboratory; 4$^{th}$ Annual California Biomass Collaborative Forum, Mar. 27, 2007 (Power Point Presentation).
International Search Report PCT/CA2005/001137 (Jul. 19, 2005).
Database WPI Week 199421 Derwent Publications Ltd., London, GB; AN 1994-174396 XP002475261 & PT 100 794 A (LNETI Lab Nacional Engenharia & Technolog) May 31, 1994 (abstract only).
J. H. Walsh, "The Synthesis of Atmospherically-Neutral Methanol Integrated with the Generation of Electricity in Processes Equipped for the Capture and Sequestering of Carbon Dioxide", *Energy Conversion and Management*, Elsevier Science Publishers, Oxford, GB, 1993, pp. 1031-1049, XPOO2087641 ISSN: 0196-8904.
*The International Preliminary Report on Patentability*, International application No. PCT/US2007/008560, Oct. 28, 2008, 11 pages.
Cambridge Recycling & Energy Systems, Co., *Document*, CareCo, 1994.

(Continued)

*Primary Examiner* — Jafar Parsa

(74) *Attorney, Agent, or Firm* — Sunstein Kann Murphy & Timbers LLP

(57) ABSTRACT

A method and apparatus for synthesizing ethanol using synthetic routes via synthesis gas are disclosed. A method and apparatus for gasifying biomass, such as biomass, in a steam gasifier that employs a fluidized bed and heating using hot flue gases from the combustion of synthesis gas is described. Methods and apparatus for converting synthesis gas into ethanol are also disclosed, using stepwise catalytic reactions to convert the carbon monoxide and hydrogen into ethanol using catalysts including iridium acetate.

34 Claims, 11 Drawing Sheets

U.S. PATENT DOCUMENTS

| | | | | |
|---|---|---|---|---|
| 5,900,505 | A | 5/1999 | Tustin | 562/519 |
| 5,917,089 | A | 6/1999 | Howard | 562/519 |
| 5,922,090 | A | 7/1999 | Fujimura | 48/197 R |
| 5,922,092 | A | 7/1999 | Taylor | 55/295 |
| 5,932,764 | A | 8/1999 | Morris et al. | 562/519 |
| 5,980,858 | A | 11/1999 | Fujimura | 423/655 |
| 5,993,751 | A | 11/1999 | Moriarty | 422/233 |
| 6,002,054 | A | 12/1999 | Ueoka | 568/885 |
| 6,028,119 | A | 2/2000 | Kokubu | 518/713 |
| 6,048,374 | A | 4/2000 | Green | 48/209 |
| 6,063,355 | A | 5/2000 | Fujimura | 423/359 |
| 6,114,279 | A | 9/2000 | Fukui | 502/342 |
| 6,127,432 | A | 10/2000 | Wegman | 518/715 |
| 6,133,328 | A | 10/2000 | Lightner | 518/700 |
| 6,190,429 | B1 | 2/2001 | Fujimura | 48/197 R |
| 6,207,865 | B1 | 3/2001 | Breitscheidel | 568/705 |
| 6,211,405 | B1 | 4/2001 | Cheung | 562/519 |
| 6,283,048 | B1 | 9/2001 | Fujinami | 110/346 |
| 6,350,288 | B1 | 2/2002 | Hirayama | 48/197 R |
| 6,353,132 | B1 | 3/2002 | Zoeller | 562/519 |
| 6,355,595 | B1 | 3/2002 | Zoeller | 502/312 |
| 6,355,837 | B1 | 3/2002 | Zoeller | 562/519 |
| 6,387,842 | B1 | 5/2002 | Wegman | 502/300 |
| 6,395,927 | B1 | 5/2002 | Patois | 562/517 |
| 6,455,011 | B1 | 9/2002 | Fujimura | 422/139 |
| 6,470,833 | B1 | 10/2002 | Hyppanen | 122/4 D |
| 6,486,366 | B1 | 11/2002 | Ostgard | 568/863 |
| 6,521,783 | B1 | 2/2003 | Wegman | 560/232 |
| 6,596,781 | B1 | 7/2003 | Schinski | 518/700 |
| 6,613,111 | B2 | 9/2003 | Paisley | 48/89 |
| 6,642,413 | B2 | 11/2003 | Thiebaut | 562/519 |
| 6,645,442 | B2 | 11/2003 | Kaneko | 422/187 |
| 6,647,903 | B2 | 11/2003 | Ellis | 110/348 |
| 6,676,716 | B2 | 1/2004 | Fujimura | 48/197 FM |
| 6,680,137 | B2 | 1/2004 | Paisley | 429/19 |
| 6,683,224 | B1 | 1/2004 | Hourticolon | 568/864 |
| 6,723,886 | B2 | 4/2004 | Allison | 568/909 |
| 6,736,955 | B2 | 5/2004 | Shaw | 205/450 |
| 6,747,067 | B2 | 6/2004 | Melnichuk et al. | 518/702 |
| 6,779,492 | B2 | 8/2004 | Baglione | 122/4 D |
| 6,802,890 | B2 | 10/2004 | Hyppanen | 95/271 |
| 6,808,543 | B2 | 10/2004 | Paisley | 48/197 R |
| 6,830,597 | B1 | 12/2004 | Green | 48/209 |
| 6,837,910 | B1 | 1/2005 | Yoshikawa | 48/197 FM |
| 6,846,951 | B1 | 1/2005 | Thiebaut | 562/519 |
| 6,863,878 | B2 | 3/2005 | Klepper | 423/650 |
| 6,916,951 | B2 | 7/2005 | Tustin | 560/231 |
| 6,916,952 | B1 | 7/2005 | Le Berre | 560/232 |
| 6,949,224 | B1 | 9/2005 | Miyoshi | 422/139 |
| 6,959,654 | B2 | 11/2005 | Abrams | 110/345 |
| 6,972,114 | B2 | 12/2005 | Pope | 422/139 |
| 6,991,769 | B2 | 1/2006 | Kaneko et al. | 422/187 |
| 6,997,118 | B2 | 2/2006 | Chandran | 110/212 |
| 7,008,967 | B2 | 3/2006 | Keyser et al. | 518/702 |
| 7,009,070 | B2 | 3/2006 | Thiebaut | 560/232 |
| 7,067,558 | B2 | 6/2006 | Grobys | 518/700 |
| 7,087,097 | B1 | 8/2006 | Karl | 48/76 |
| 7,094,264 | B2 | 8/2006 | Steer | 48/198.7 |
| 7,115,774 | B2 | 10/2006 | Magna | 562/519 |
| 7,128,004 | B2 | 10/2006 | Miyoshi | 110/101 R |
| 7,166,268 | B2 | 1/2007 | Fukunaga | 423/651 |
| 7,169,821 | B2 | 1/2007 | Branson | 518/702 |
| 2002/0095866 | A1 | 7/2002 | Hassett | 48/199 FM |
| 2003/0008928 | A1 | 1/2003 | Klepper | 518/704 |
| 2003/0092945 | A1 | 5/2003 | Seiki | 568/700 |
| 2003/0115800 | A1 | 6/2003 | Yamada et al. | 48/197 |
| 2003/0138365 | A1 | 7/2003 | Obidniak et al. | 422/224 |
| 2003/0202912 | A1 | 10/2003 | Myohanen | 422/143 |
| 2004/0055216 | A1 | 3/2004 | Berger | 48/197 FM |
| 2004/0060236 | A1 | 4/2004 | Yoshikawa | 48/63 |
| 2004/0107638 | A1 | 6/2004 | Graham | 48/197 |
| 2004/0180971 | A1 | 9/2004 | Inoue | 518/702 |
| 2004/0247499 | A1 | 12/2004 | Matsuoka | 422/191 |
| 2005/0095183 | A1 | 5/2005 | Rehmat | 422/188 |
| 2005/0107482 | A1 | 5/2005 | Van Egmond et al. | 518/726 |
| 2005/0112037 | A1 | 5/2005 | Darling | 422/139 |
| 2006/0009537 | A1 | 1/2006 | Iordache-Cazana | 518/703 |
| 2006/0075946 | A1 | 4/2006 | Gounder | 110/346 |
| 2006/0150510 | A1 | 7/2006 | Hiltunen | 48/210 |
| 2006/0165589 | A1 | 7/2006 | Nielsen | 423/656 |
| 2006/0196398 | A1 | 9/2006 | Graham | 110/267 |
| 2007/0010588 | A1 | 1/2007 | Pearson | 518/701 |
| 2007/0010589 | A1 | 1/2007 | Pearson | 518/702 |
| 2007/0022924 | A1 | 2/2007 | Hyppanen | 110/245 |
| 2007/0027220 | A1 | 2/2007 | Lattner | 518/726 |

FOREIGN PATENT DOCUMENTS

| | | |
|---|---|---|
| CA | 2456825 | 3/2003 |
| CN | 1477090 | 2/2004 |
| CN | 1563790 | 1/2005 |
| CN | 2745924 Y | 12/2005 |
| CN | 1730611 | 2/2006 |
| CN | 2789258 Y | 6/2006 |
| CN | 2813616 Y | 9/2006 |
| EP | 0 167 300 A1 | 1/1986 |
| EP | 0 335 625 A2 | 10/1989 |
| GB | 2 162 172 A | 1/1986 |
| JP | 2003268390 | 9/2003 |
| JP | 2004051718 | 2/2004 |
| JP | 2004149556 | 5/2004 |
| JP | 2005112956 | 4/2005 |
| JP | 2005132739 | 5/2005 |
| JP | 2006083293 | 3/2006 |
| JP | 2006131820 | 5/2006 |
| KR | 20010062259 | 7/2001 |
| TW | 292046 Y | 6/2006 |
| WO | WO 03/097847 | 11/2003 |
| WO | WO 2006/021017 | 2/2006 |
| WO | WO 2006/123018 | 11/2006 |
| WO | WO 2006/123146 | 11/2006 |

OTHER PUBLICATIONS

D. Dayton, *NREL Presentation*, 4th Annual California Biomass Collaborative Forum, Mar. 27, 2007.

Cambridge Recycling & Energy Systems, Co., *Maverick County Texas Plant*, CareCo, 1980.

Cambridge Recycling & Energy Systems, Co., *Quincy, Florida Gasifier*, CareCo, disclosed 1986.

Cambridge Recycling & Energy System, Co. (?), *Process Flow Diagram for Eastman Methanol Reactor*, CareCo, 1980.

Austrian Energy Agency, *Case Study: 2 MWel biomass gasification plant* in Güssing (Austria), Apr. 2004.

Invitation to Pay Additional Fees from the International Search Authority dated Oct. 26, 2007 (International application No. PCT/US2007/008560).

Sunggyu Lee et al., "Liquid phase methanol and dimethyl ether synthesis from syngas," Topics in Catalysis, vol. 32, Nos. 3-4, pp. 197-207 (Mar. 2005).

Hye-Won Lim et al., "Modeling of the Kinetics for Methanol Synthesis using $Cu/ZnO/Al_2O_3/ZrO_2$ Catalyst: Influence of Carbon Dioxide during Hydrogenation," Ind. Eng. Chem. Res., vol. 48, pp. 10448-10455 (2009).

Sunggyu, Lee et al., "Effects of Carbon Dioxide and Water on the Methanol Synthesis Catalyst," Energy & Fuels, vol. 3, pp. 2-7 (1989).

SYSTEM AND METHOD FOR CONVERTING BIOMASS TO ETHANOL VIA SYNGAS

CROSS REFERENCE TO RELATED APPLICATIONS

This application claims priority from provisional application 60/789,067 filed on Apr. 5, 2006, and from provisional application 60/881,189, filed Jan. 19, 2007.

TECHNICAL FIELD

This invention relates to processes for syngas and in particular a method of producing ethanol from biomass. This process relates to the production of ethanol (ethyl alcohol) from biomass materials. The yield of ethanol is maximized by the selection of efficient catalytic steps.

BACKGROUND

Synthesis gas, or "syngas," is the name given to a gas mixture that contains varying amounts of carbon oxides (such as carbon monoxide) and hydrogen. The name comes from their use as intermediates in creating synthetic natural gas, ammonia, methyl alcohol (methanol), or fuels.

Syngas can be generated in many ways, for example, by the gasification of a carbon containing fuel to a gaseous product with a heating value, e.g., gasification of coal, biomass or municipal waste materials. Other examples include the steam reforming of natural gas, methane from various sources, or liquid hydrocarbons. Syngas is combustible and often used as a fuel source or as an intermediate for the production of other chemicals. Syngas is also used as an intermediate in producing synthetic petroleum for use as a fuel or lubricant via catalysis using a Fisher-Tropsch catalyst. Syngas for use as a fuel is most often produced by gasification of coal or municipal waste.

When used as an intermediate in the large-scale, industrial synthesis of hydrogen and ammonia, it is also produced from natural gas (via the steam reforming reaction). The syngas produced in large waste-to-energy gasification facilities is used as fuel to generate electricity. Coal gasification processes are reasonably efficient and were used for many years to manufacture what used to be known as "illuminating" gas, or coal gas, for lighting in street lamps and homes before electricity became widely available.

Synthesis gas is widely used to produce methanol. Synthesis gas from coal is also used to produce an array of chemicals. It can be catalysed to produce a class of diesel fuel called "Fisher-Tropsch fuels".

Recently, specialized bacteria have been developed to convert synthesis gas into a mixture of ethanol and acetic acid. The chemical pathway to ethanol is not efficient in these one-step processes.

There have also been disclosed a number of methods for synthesizing ethanol directly from biomass using fermentation or other biological processes. While these processes have been used to produce ethanol from the cellulose contained in biomass, such processes are severely limited by, among other things, their inability to convert the lignins contained in lignocellulosic biomass to useful products.

Disclosed is a process by which synthesis gas is efficiently converted into ethanol, requiring little purification and water removal. This ethanol is suitable as an alternative fuel, for industrial use, as a chemical precursor, or as an additive in pharmaceuticals or beverages.

Ethyl alcohol (ethanol) is a global product which is used for beverages, industrial processes and more recently as a fuel for combustion engines which is cleaner burning than gasoline.

Because the world demand for ethanol is so great and will now grow incredibly with the attempt to use it as a fuel additive on a large scale here in North America, a process that utilizes whole biomass would increase global ethanol capacity.

The subject invention describes a method by which the synthesis gas which is produced from biomass material can be efficiently converted into ethanol.

SUMMARY OF THE INVENTION

The present invention is a method of producing ethanol from syngas comprising the steps of:
providing syngas;
converting the syngas into methanol to produce methanol and carbon monoxide and hydrogen;
reacting an catalyst and a promoter with the methanol, carbon monoxide and hydrogen to produce a mixture comprising methyl acetate, hydrogen, methanol, acetic acid, and water;
separating the mixture to separate the promoter, a mixture of methyl acetate and methanol, and a mixture of acetic acid and water;
adding hydrogen to the methyl acetate and methanol mixture and reacting the mixture with a hydrogenation catalyst to produce ethanol.

Another process is disclosed which converts syngas into ethanol. Syngas is converted to a mixture of methanol, carbon monoxide and hydrogen; the methanol and carbon monoxide mixture is reacted using a catalyst to produce acetic acid and carbon monoxide, acetic acid is reacted with ethanol in the presence of a catalyst to produce a mixture comprising ethyl acetate and water; and the ethyl acetate is reacted with the hydrogen using a hydrogenation catalyst to produce ethanol.

A process is disclosed that converts synthesis gas (syngas) produced from biomass material into ethyl alcohol. Biomass is gasified to produce syngas in a steam gasifier, the syngas is compressed and reacted with one or more catalysts to produce ethanol. The biomass gasifier in this invention is a box-shaped vessel having a bottom that is a distribution plate and tubes, where the tubes carry hot gases so as to heat the fluidized bed. Each catalytic step would be accomplished using best method available and is a catalytic step requiring a catalyst, a vessel, and appropriate heat and pressure.

A method for producing synthesis gas from dried biomass using steam gasification with a fluidized bed is disclosed. The bed is in a boxlike vessel with a distributor plate for a floor, hot gases are transmitted through tubes, and biomass is injected to gasify to syngas. In a further embodiment of this invention, the gasification process is heated by the burning of low BTU synthesis gas produced in a second, air blown gasifier.

An apparatus for producing ethanol from synthesis gas is also disclosed, wherein such apparatus includes a methanol reactor, a methyl acetate reactor with a metal catalyst, a distillation apparatus for separating out methyl acetate, acetic acid, hydrogen, and methyl iodide, and an ethanol reactor that produces methanol. In a further embodiment of this invention, the apparatus for producing ethanol receives synthesis gas from a steam gasifier with a fluidized bed having dried biomass as a fuel.

A method for producing ethanol from biomass is also disclosed, such method including providing syngas, converting the syngas to a mixture containing methanol, reacting the mixture comprising methanol to obtain a mixture comprising methyl acetate and methanol; and reacting the mixture comprising methyl acetate and methanol with hydrogen to produce ethanol.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Definitions. As used in this description and the accompanying claims, the following terms shall have the meanings indicated, unless the context otherwise requires:

As used herein, the terms "comprises" and "comprising" are to be construed as being inclusive and opened rather than exclusive. Specifically, when used in this specification including the claims, the terms "comprises" and "comprising" and variations thereof mean that the specified features, steps or components are included. The terms are not to be interpreted to exclude the presence of other features, steps or components.

Figure 1A:
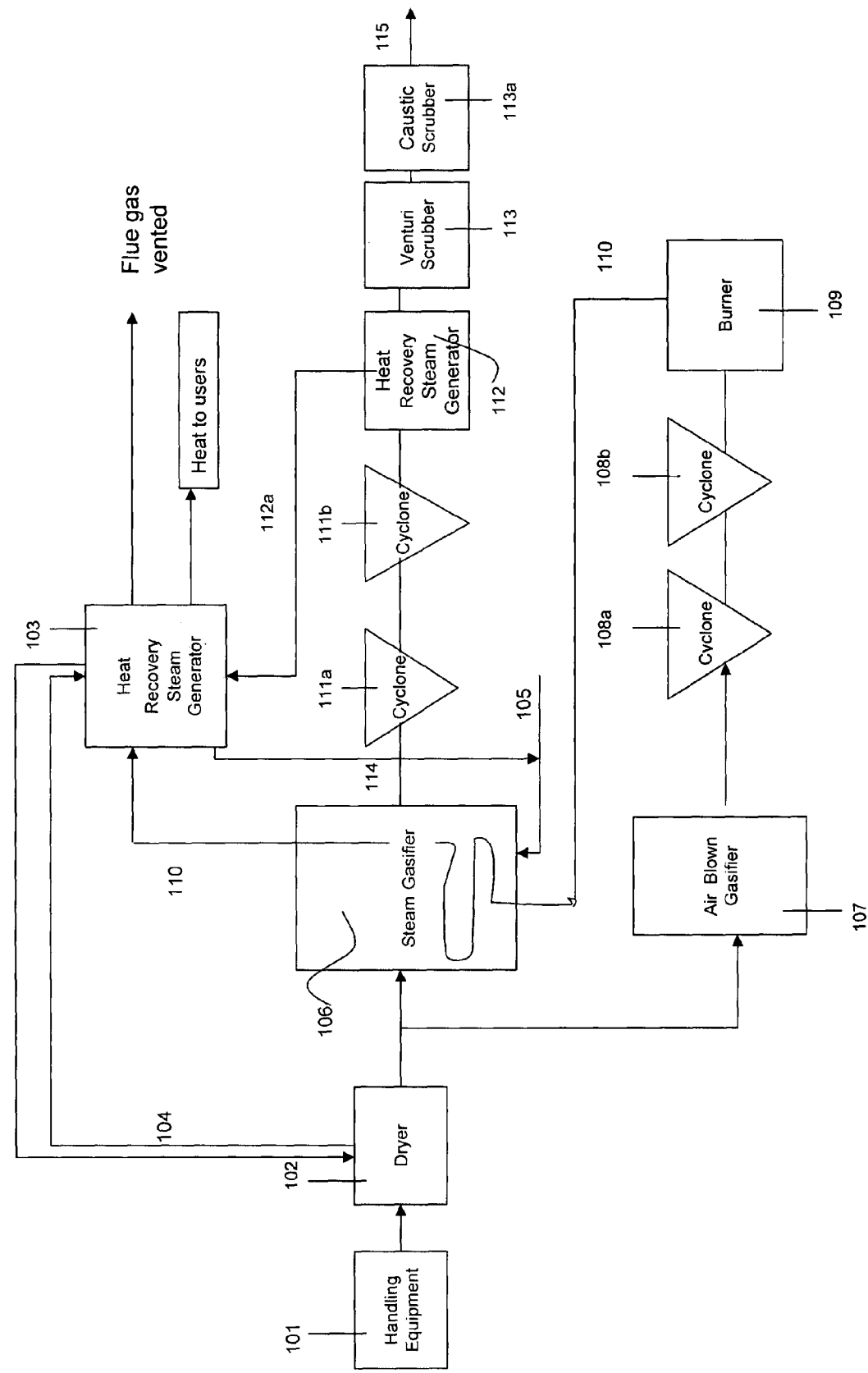
FIG. 1A is a schematic view of a preferred embodiment of the process for producing syngas from biomass, a process of the present invention.

As a first preferred embodiment, biomass is converted to ethanol. Referring to FIG. 1A, the biomass handling equipment 101 and dryers 102 are the first steps in the process. The biomass handling equipment 101, for example a grinder, takes raw biomass and processes it into a size suitable for gasification. In most instances, the biomass must be chopped, ground, hogged or chipped into cubes measuring 2 inches or less.

This biomass may be dried down to 30% moisture down to 1% (preferably 20% or less) using a pressurized steam dryer 102, for example, a steam dryer supplied by BMA (Niro). The dryer 102 provides steam at a pressure of approximately 275 kPa (with a range between 225 and 325 kPa). The dried biomass, with less than 30% moisture, is then discharged via a conveyor to the dry feedstock storage bin (not shown).

Water vapour 104 from the wet biomass is recovered from the steam dryer 102 at 275 kPa and this is superheated to supply fluidization steam 105 for the steam gasifier 106. This may be accomplished by passing it through a heat recovery steam generator 103 where it is heated by the hot flue gases 110 exiting the steam gasifier 106.

A portion of the dried biomass is fed to the air-blown gasifier 107 and a low BTU syngas 107a is produced. This low BTU syngas 107a may be cleaned in two cyclones 108a and 108b to remove any particulate matter. The cleaned low BTU syngas 107b is then burned in a low BTU gas burner 109 to produce high temperature flue gas 110. This flue gas, which exits the burner at about 1090 degrees Celsius (in a range of 1000 to 1200 degrees Celsius) provides heating to the steam gasifier 106 through an internal heat exchanger 202. As an alternate embodiment, the burner 109 can burn other fuels to produce flue gas, including methane, landfill gas, natural gas, or methane and other light hydrocarbons produced by the anaerobic digestion of manures or biosolids.

Figure 3:
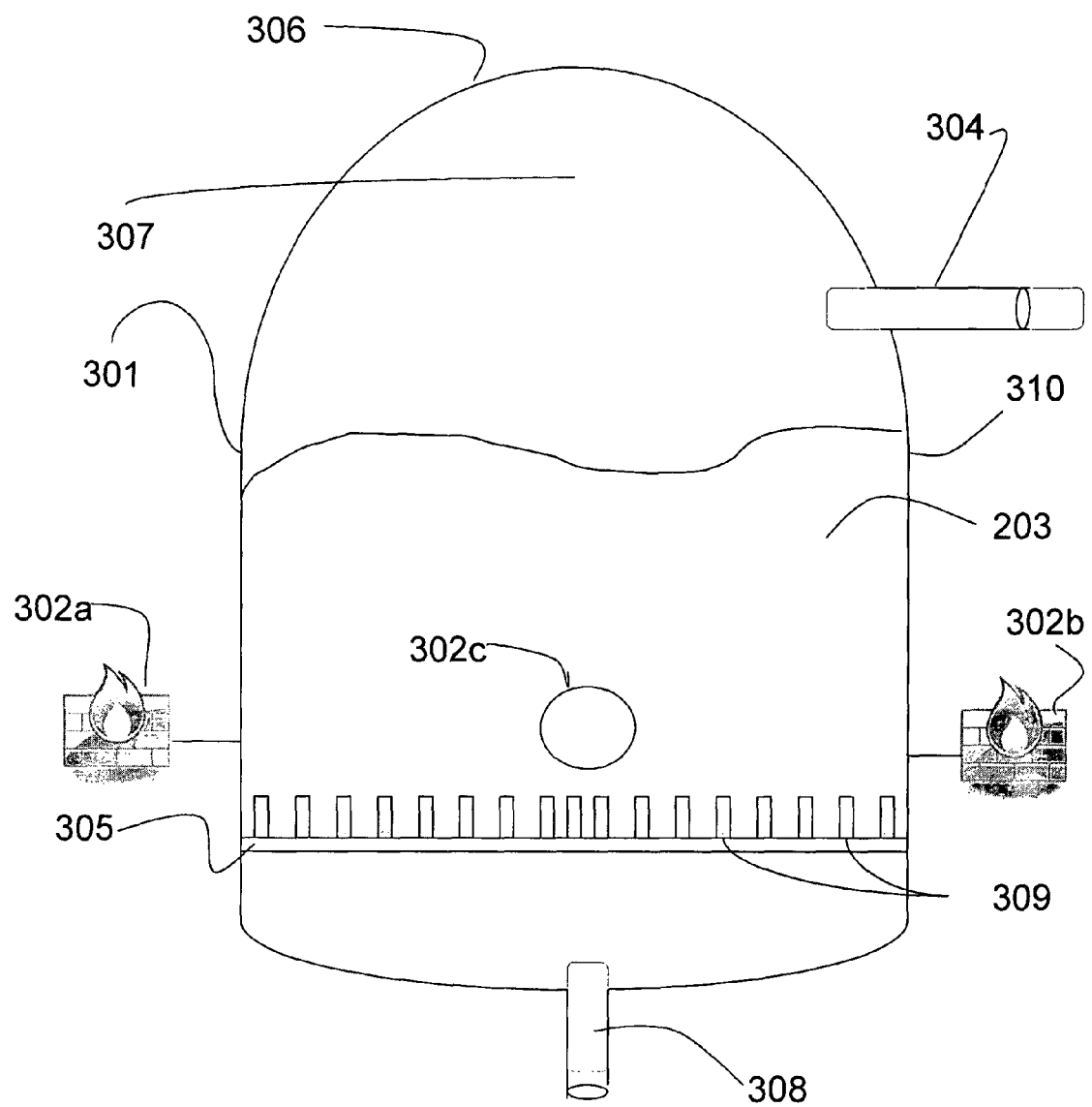
FIG. 3 is a drawing showing a view of the air blown gasifier, an apparatus of the present invention.

One embodiment of an air-blown gasifier utilized here, as illustrated in FIG. 3, has proven commercial success in a 1,000 ton per day gasification plant in Quincy, Fla. The air blown gasifier can be a vessel 301 constructed with an exterior of a metal such as carbon steel, with an interior refractory lining sufficient to withstand the temperatures within. In one embodiment, the vessel 301 is cylindrical in shape with vertical walls 310 and a ceiling 306. A preferred embodiment is a domed ceiling. A typical vessel would be approximately 8 feet in diameter and 40 feet in height, though the design is capable of being scaled up or down.

In the preferred embodiment, the vessel 301 has a distributor plate 305 as its floor and an outlet 304 set either in the ceiling or in an upper portion of the vertical wall 310. The reactor has a bed 303 of silica sand or similar mineral at the bottom, the silica sand typically having a particle size of 300 to 400 microns. The gasifier chamber is loaded with bed material, leaving a freeboard space 307 between the top of the fuel pile and the ceiling.

The distributor plate 305 has a series of holes bored into it, each of which has attached (by threading, welding or some other secure mounting technique) metal capped cylinders 309. Each of these cylinders is hollowed out at the bottom so as to draw pressurized air 308a from a plenum 308 beneath the plate 305.

The plenum 308 is a chamber in which pressurized air is fed under the distributor plate 305. In a typical embodiment, this will be a chamber in an upside down dome shape that encompasses the entire distributor plate, and has an entry for air.

Pressurized air 308a is directed into the plenum beneath the distribution plate and is forced through the capped cylinders 309 into the bed, causing fluidization of the bed. The arrangement of the cylinders on the distributor plate 305 is designed so as to evenly fluidize the material throughout the bed. There are a number of configurations that can be used to achieve this. One way is to install cylinders 309 in a gridlike pattern, which can be a rectilinear, triangular, or other pattern on the plate 305.

The air blown gasifier may also feature startup burners 302a, 302b, and 302c that heats the vessel to approximately 750 to 900 degrees Celsius, the operating range of the air blown gasifier. Startup burners 302a and 302b may be oriented outside the walls of the gasifier, while burner 302c may be located directly in the bed. These startup burners are shut off when the bed reaches its operating temperature, and the temperature of the bed is maintained by adding dried biomass and air to the vessel. The air blown gasifier is preferentially operated at or around atmospheric pressure, in the range of 100 to 175 kPa.

Biomass may be fed to the air gasification vessel 301 by a tapered screw feeder 303, which feeds dried biomass into the middle of the bed 302 when the bed is fluidized, and on top of the bed when the bed is not fluidized. The tapered screw feeder 311 is designed such that the biomass is compacted as it progresses through the screw, resulting in a plug of wood 311a near its opening into the vessel that prevents back pressure to the vessel.

The bed 303, when fluidized, is maintained at a level below the ceiling 306 to maintain sufficient freeboard space 307 such that no bed materials such as silica sand, escape with the low BTU syngas through the outlet 304. Ideally, the conditions of the vessel are maintained so that effluent gases produced have at least a two second residence time in the freeboard space before they exit through the outlet, with a range between 1 and 5 seconds. In a typical embodiment, where the diameter is 8 feet and the height is 40 feet, the bed will have a height of less than 15 feet when fluidized, and less than 6 feet when static.

Returning to the preferred system embodiment, shown in FIG. 1A, the flue gas 110 produced by the burner 109 is transferred to the internal heat exchanger 202 of steam gasifier 106.

Figure 2:
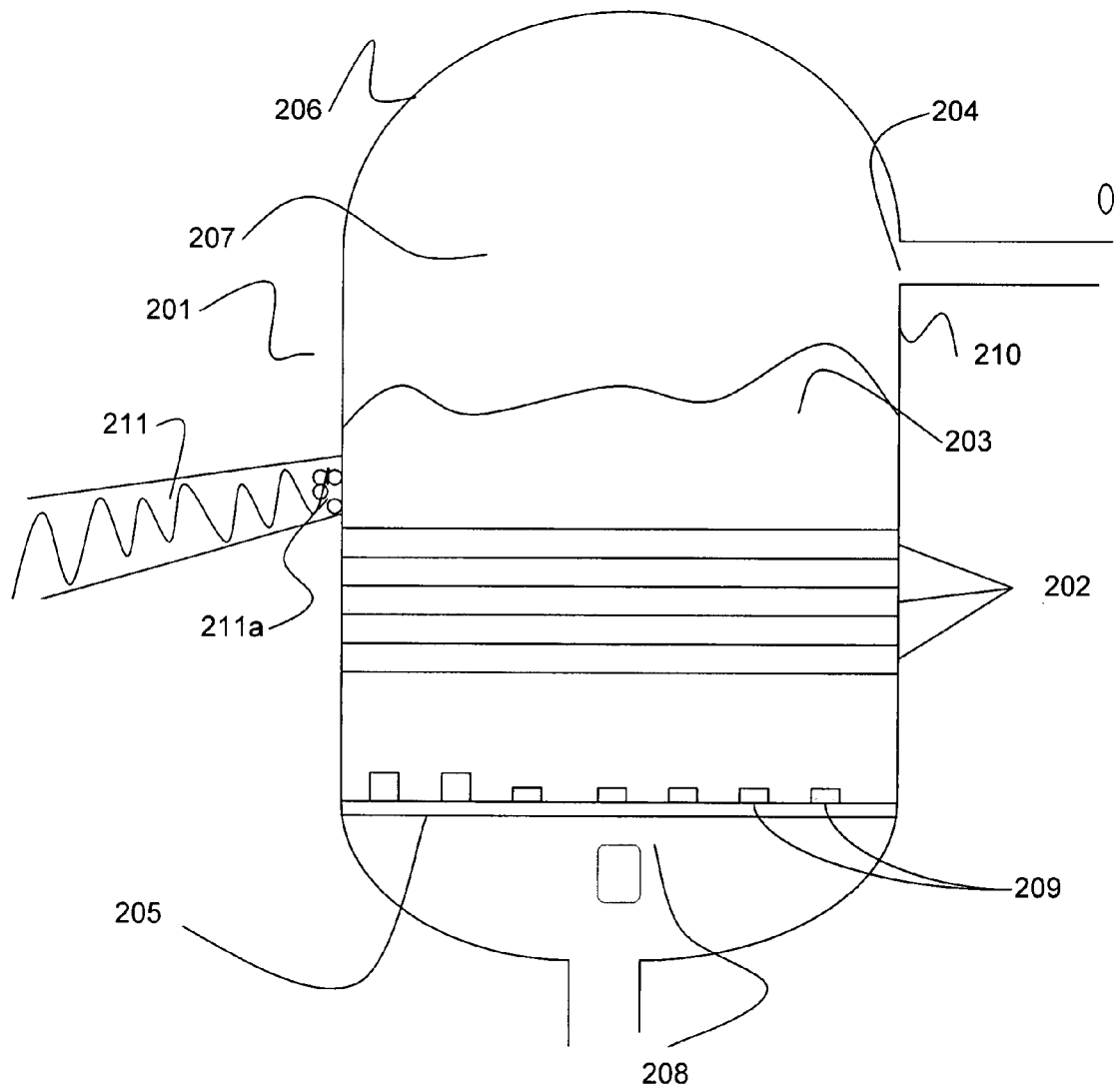
FIG. 2 is a drawing showing an end view of the steam gasifier, an apparatus of the present invention.

A preferred embodiment of a biomass steam gasifier 106 is a proprietary fluidized bed system, as illustrated in FIG. 2. The design of the reactor is a box-shaped vessel 201, having walls 210 and a ceiling 206, a typical embodiment having length of 20 feet, width 10 feet, and height between 30 and 40 feet, though many other configurations and scales are possible. A distributor plate 205 is the floor. In a typical embodiment, the ceiling 206 is in the shape of a dome or a semicylinder. In the distribution plate 205 are bored holes in which are installed capped cylinders 209 capable of drawing steam from a plenum 208 beneath the distributor plate 205 into the bed 203 in a direction parallel to the plane of the distributor plate. Like the air blown gasifiers, these capped cylinders have a hollowed out inlet communicating with the space beneath the distributor plate, and has one or more outlet holes transverse to the longitudinal axis of the cylinder. In this embodiment, superheated steam in a range of 500 to 600 degrees Celsius is forced into the plenum 208 beneath the distributor plate and is forced out the capped cylinders 209 into the bed 203, in a manner that evenly fluidizes the bed. In other embodiments, non-superheated steam may be used to fluidize a bed and promote gasification. The capped cylinders may be screw threaded, welded, or otherwise securely mounted into the openings of the distributor plate.

The plenum 208 is a chamber in which superheated steam is fed under the distributor plate. In a typical embodiment, this will be a chamber in an upside down dome shape that encompasses the entire distributor plate, and has an entry for steam.

Figure 5:
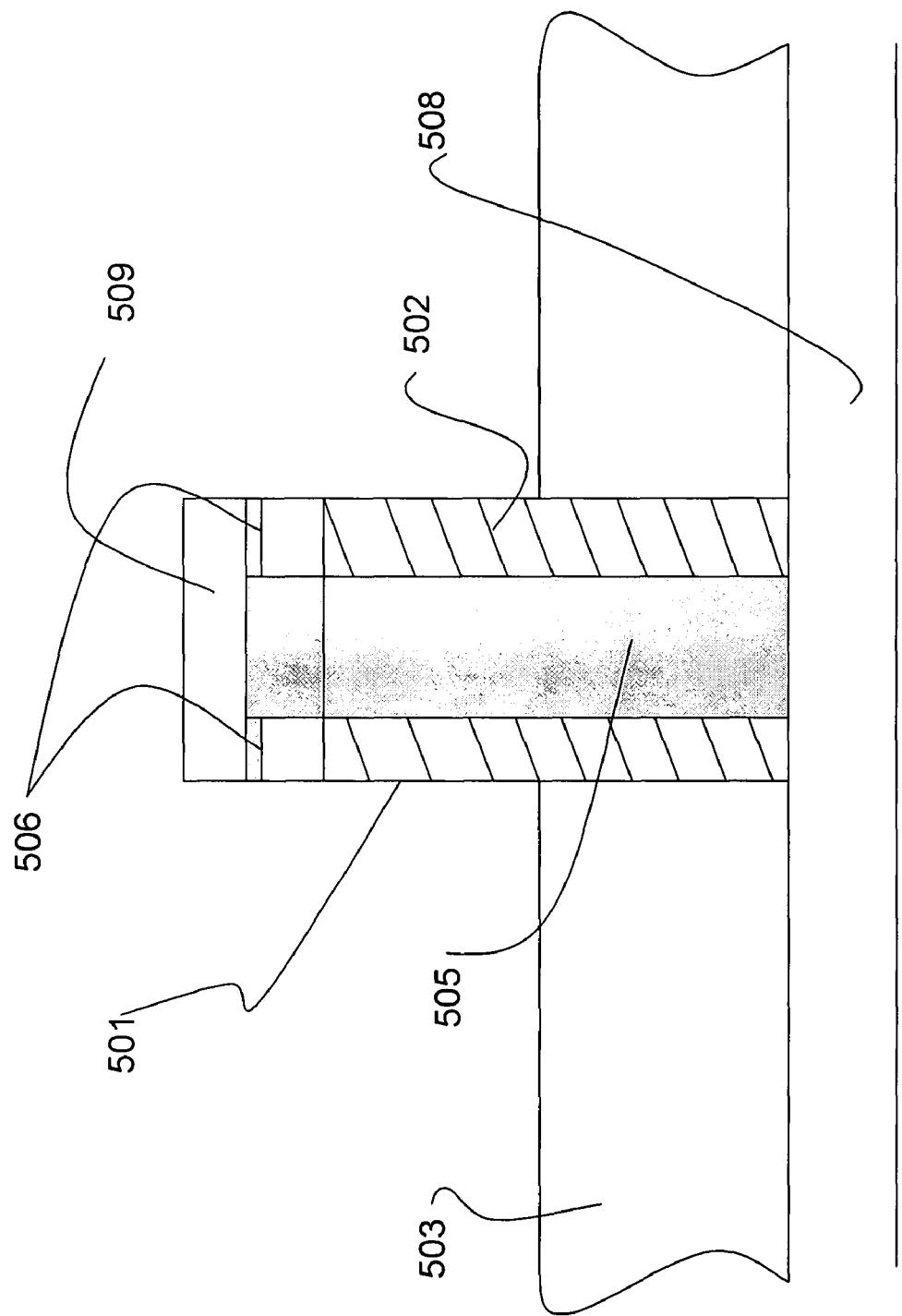
FIG. 5 is a drawing of a capped cylinder in the distribution plate used in the air-blown and steam gasifiers of this invention.

An example of such a cylinder that can be used either in an air-blown or steam gasifier can be seen in FIG. 5, a cross section of a distribution plate and plenum. The plate 503 has a gap that is filled by a cylinder 501 mounted into the plate. Typically, the cylinder 501 has a length of about six inches, of which 1 to 4 inches are mounted above the distributor plate. The distributor plate is generally constructed of carbon steel, with a thickness of approximately one half inch. The cylinder in this embodiment is mounted using threading 502, though other mountings, such as welding can be used. The cylinder has a cap 506 that is threaded onto the cylinder. Underneath the plate 503 is a plenum 508 through which either superheated steam or air are distributed to the cylinders. The steam or air enters the hollowed area 505 through the cylinder. This hollowed area has an inner diameter in the range of ¼ to 1 inch, preferably one half inch. This hollowing is directed to one or more small outlet holes 506 drilled transverse to the axis of the cylinder, so as to allow the passage of steam or air into the bed 507 in a direction parallel to the plane of the distributor plate 505. In this embodiment, the cap 509 of the cylinder, and thus the outlet holes 506, extends anywhere from 1 inch to 5 inches above the distributor plate 503. The outlet holes in a preferred embodiment have an inner diameter between ¹⁄₁₆ and ¼ of an inch. By constricting the outflow of gas, the cylinder provides enough force to fluidize the bed material.

Returning to FIG. 2, the bed 203 consists of a mineral, for example, granular silica sand and/or dolomite (which inhibits tar formation) or olivine or a combination thereof, that may also have ceramic balls on top of the bed to hold the silica in place in the vessels. Biomass feedstock is injected into the steam gasifier bed 203 using a tapered screw feeder 211. This tapered screw feeder, by its action in compressing the biomass produces a plug of biomass 211a at its outlet, which prevents the entrance of air into the vessel 201 and prevents back pressure from gases inside the vessel. It is important that the biomass be substantially air-free to prevent unwanted chemical reactions involving nitrogen throughout the process. This screw feeder is oriented so that biomass is injected in the middle of the bed when the bed is fluidized, and on top of the bed 203 when the bed is not fluidized.

The bed and wood feed stock is added so that the gasifier vessel is maintained at an optimal level. The amount of freeboard space 207 between the bed 203 and the ceiling 206 is maintained at a level so that, when fluidized, none of the minerals from the bed are ejected out of the vessel. Ideally, the residence time of gases in the freeboard space is in the range of one to five seconds, preferably two seconds. The extended residence time allows reactions such as the water gas shift (which converts CO into H2 and CO2) and steam reformation to occur, thus maximizing the output of hydrogen. It is important that the biomass be substantially air-free to prevent unwanted chemical reactions involving nitrogen throughout the process.

Superheated steam 105, heated to a temperature between 500 and 600 degrees Celsius (preferably 550 degrees Celsius), which may come from the heat recovery steam generator 103, is injected into the steam gasifier bed through the plenum 208 under the distributor plate 205 and through the capped cylinders 209. The steam is injected at a sufficient pressure to fluidize the bed evenly. Non-superheated steam may also be used to fluidize the bed and promote gasification.

Figure 4:
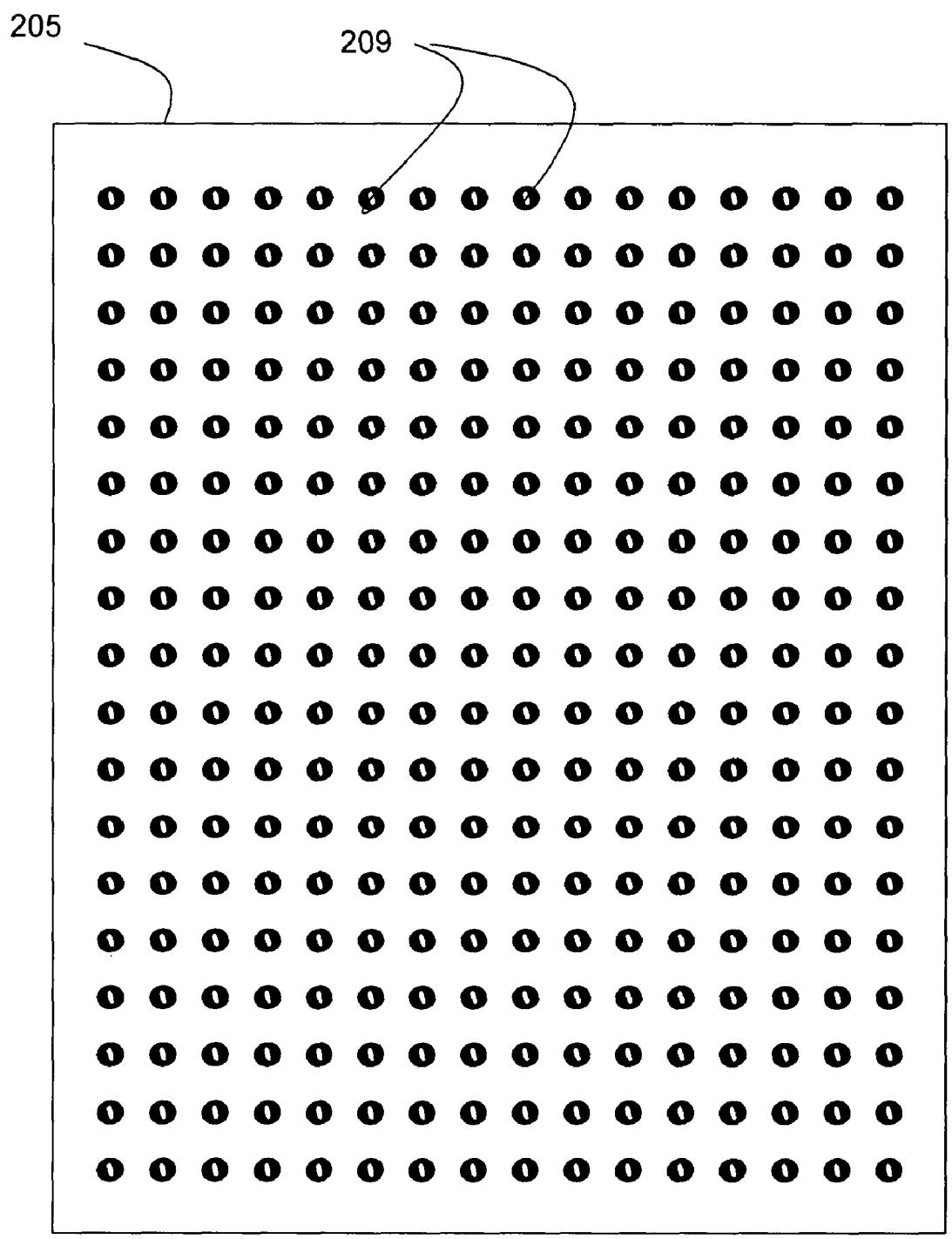
FIG. 4 is a drawing of a distribution plate used in the air-blown and steam gasifiers used in a process of the invention.

An example of the orientation of the capped cylinders 209 on the distributor plate 205 can be seen in FIG. 4, which is a top down view of a distributor plate 205. The bolts 209 are arranged evenly around the plate, in a gridlike pattern that may be rectilinear, as shown, or triangular, or some other regular arrangement. Typically, the capped cylinders are at a distance between 1 inch and 6 inches from one another, preferably 2 inches. In this manner, the entire area of the bed is evenly fluidized. A similar pattern may be used for the distributor plate 305 of the air blown gasifier.

Returning to FIG. 2, the bed 203 is heated through an internal heat exchanger 202, that consists of a plurality of stainless steel tubes running across the axis of the fluidized bed to transfer heat from the hot flue gas 110, which exits the burner at a temperature of about 1090 degrees Celsius (in a range of 1000 to 1200 degrees Celsius), to the fluid bed 203 of the steam gasifier. In this manner, the bed is maintained at a temperature of approximately 815 degrees Celsius, with a range of 750 to 900 degrees Celsius. In FIG. 2 (side view), it can be seen that heat exchanger tubes 202 extend the length of the gasifier and carry the hot flue gases from the burner 109.

Figure 2A:
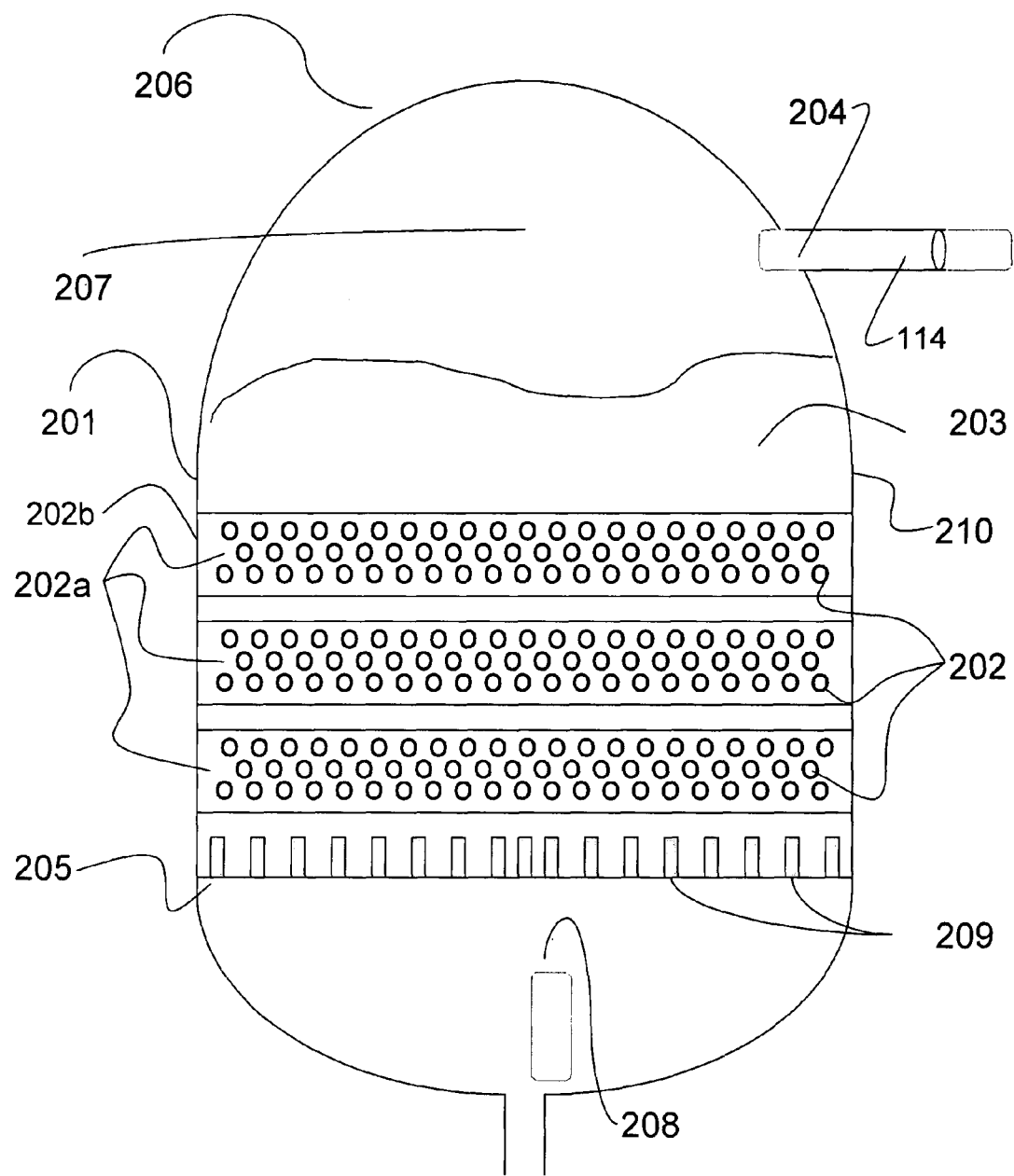
FIG. 2A is a drawing showing a side view of the steam gasifier, an apparatus of the present invention.

FIG. 2A, an end view of the steam gasifier, shows how the tubes are arranged in the bed. The tubes 202 are arranged in bundles 202a that extend across the width of the vessel 201. These bundles, are held together by supports 202b that are anchored in the walls or the ceiling and which maintain the tubes in position. The tubes are held together with the supports in such a manner that they can be easily removed from the gasifier as a group for cleaning and maintenance. The tubes typically are composed of stainless steel or similar materials. The tubes have an inner diameter between one half and 4 inches, preferably 1.5 to 3 inches.

In the preferred embodiment, the bundles 202a of tubes are composed of rows of tubes wherein the rows are staggered with one another so that, looking down the ends of the tubes, the tubes form triangular arrangements with respect to one another. In this configuration, the tubes assist not only in the heating of the fluidized bed, but in the flow of gases through the bed. This is accomplished by the fact that rising gases must constantly strike the tube surfaces as they travel upward, thereby breaking up large gas bubbles and forming smaller ones, which improves the mixing of gases with the bed materials throughout the bed.

In a preferred arrangement, the first bundle of tubes is set approximately from two to four feet from the bottom of the bed, as marked by the distributor plate. A second bundle, if necessary, is placed two to four feet above the first bundle, and a third (if necessary) two to four feet above the second bundle. The number of bundles necessary depends on many factors, including the size of the vessel, the heat transfer coefficient, the flue gas temperature. In this manner, the fluid bed is heated throughout its depth. In a typical arrangement, the rows are spaced so that the centers of the tubes are approximately 6 inches apart, so that at 10 foot wide gasifier vessel would have rows of 20 tubes. The tube bundles may have anywhere from 2 to 6 of these rows, staggered with each other as described above so as to maximize the surface contact of rising gases.

Figure 7:
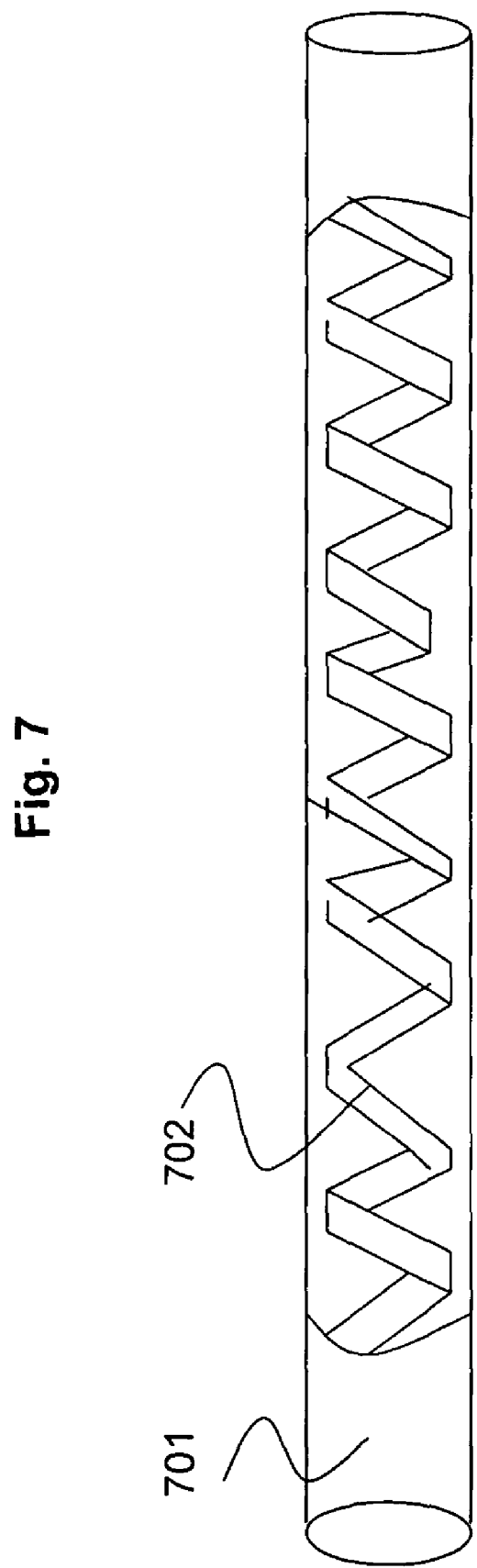
FIG. 7 is a cutaway view of a heating tube of a steam gasifier.

The number of tubes required is highly dependent on the inlet flue gas temperature, as well as the nature of the biomass, the heat transfer coefficients of the tubes and the bed material, and the desired bed temperature. The number of required tubes may be decreased by inserting strips into the tubes, as illustrated in FIG. 7. In this figure, it can be seen that tube 701, cut away contains a strip 702 that is twisted in a helix like pattern through the length of the tube. This inserted strip can be made of any heat conductive metal, and can increase the heat transfer coefficient of the tube by a factor between 2 and 10, thus decreasing the number of tubes necessary for adequate heat transfer.

The vessel is maintained at approximately atmospheric pressure, with a range between 100 and 175 kPa. Many fluidized coal fired steam boilers such as those made by Babcock & Wilcox and ABB/Combustion Engineering use in-bed heat transfer tubes to produce steam. Any volatile organics present are converted to environmentally safe components in the steam gasifier. Returning to FIG. 2, the syngas 114 produced by the steam gasifier exits through an outlet 206 in ceiling 206 at 815 degrees Celsius (range of 750 to 900 degrees Celsius).

Returning to FIG. 1, the flue gas 110 exiting the internal heat exchanger 202 of the steam gasifier 106, now at approximately 815 degrees Celsius (in a range of 750 to 900 degrees Celsius), is fed to a heat recovery steam generator 103, as shown in FIG. 1A. This generator 103 produces and heats steam using the heat provided by the flue gases. This steam may be used to produce superheated steam 105 for the steam gasifier using the steam 104 coming from the dryer, or it may produce medium pressure steam 113 for use in the dryer 102. Alternately or in addition, the steam formed may be used for external use, or for later synthetic steps, such as the steam reformer 117 or the methanol reactor 120.

The synthesis gas 114 exits the steam gasifier through the outlet 206 and passes through two cyclone separators 111a and 111b to remove essentially all particulate matter. The particulate-free syngas is cooled in a second heat recovery steam generator 112 to produce additional process steam. This process steam may be used as steam for the dryer 113, for the steam gasifier 106, reforming steam for the steam reformer 117, or water gas shift steam for the methanol reactor 120, or may be used for processes external to the plant. In a preferred embodiment, the steam 112a produced by the second generator 112 is sent to the first generator 103 to be further heated to superheated steam for the steam gasifier 106.

The hot synthesis gas is then further cleaned through a scrubbing apparatus 113. This may be accomplished using a Venturi-type wet scrubber or guard bed or some combination thereof. The scrubbing is done in a manner what leaves the syngas free of particulate matter and of compounds potentially poisonous to the catalysts which are utilized in the synthetic sequences. In particular, the syngas should be free of sulphur, metals, and nitrogen compounds. It is also desirable that the syngas composition contain a high proportion of carbon monoxide and hydrogen, and as little carbon dioxide, methane and other hydrocarbons as possible. If necessary, the syngas may also have been dried to remove water content. Lastly, the synthesis gas can be treated in a caustic scrubber 113a to remove more contaminants.

When cleaned, the synthesis gas, being composed mainly of carbon monoxide and hydrogen, with lesser amounts of carbon dioxide and small hydrocarbons such as methane, is suitable for use as a fuel, or as the starting material for a number of synthetic routes.

The synthesis gas thus produced may be used to synthesize ethanol using a number of known synthetic routes. In one embodiment, the synthesis gas produced by this biomass gasification process is contacted with a Fischer-Tropsch type catalyst to produce mixtures of ethanol and hydrocarbon products, from which the ethanol is separated using known techniques. Catalysts that may be used in this embodiment include the well known cobalt and iron catalysts, but also include other compounds such as molybdenum sulphide, tungsten sulphide, rhenium sulphide, molybdenum carbide.

In another embodiment, the synthesis gas produced by this biomass gasification process is contacted with a catalyst to produce a mixture of methanol, carbon monoxide, and hydrogen. This mixture of methanol, carbon monoxide and hydrogen is then reacted in the presence of a methanol homologation catalyst, such as ruthenium acetate, to produce a mixture containing ethanol. U.S. Pat. Nos. 4,954,665, 4,133,966, 4,111,837, 4,233,466, and 4,239,924 are incorporated here by reference.

Some examples of catalysts that may be used in this process are $Ir_4(CO)_{12}$, IrCl3, dicarbonyldiiodide rhodium, RhCl3, RhI3, RhI2(CO)2.

As an alternative to this further embodiment, the mixture of methanol, carbon monoxide and hydrogen is reacted in the presence of a carbonylation catalyst to produce a mixture comprising, in part, acetic acid and hydrogen. The carbonylation catalyst can be a heterogeneous or homogeneous catalyst based on Group VIII metals. U.S. Pat. No. 5,488,143 is incorporated here by reference. The acetic acid and hydrogen is then reacted in the presence of a hydrogenation catalyst, such as a Degussa catalyst, to produce ethanol.

In another alternative, the mixture of syngas may be reacted with a rhodium halide catalyst at a temperature between 150 and 300 degrees Celsius and at 6900 and 17000 kPa pressure to produce acetaldehyde, which may then be catalytically contacted with a hydrogenation catalyst to produce ethanol. U.S. Pat. No. 4,482,647 is incorporated here by reference.

Figure 1B:
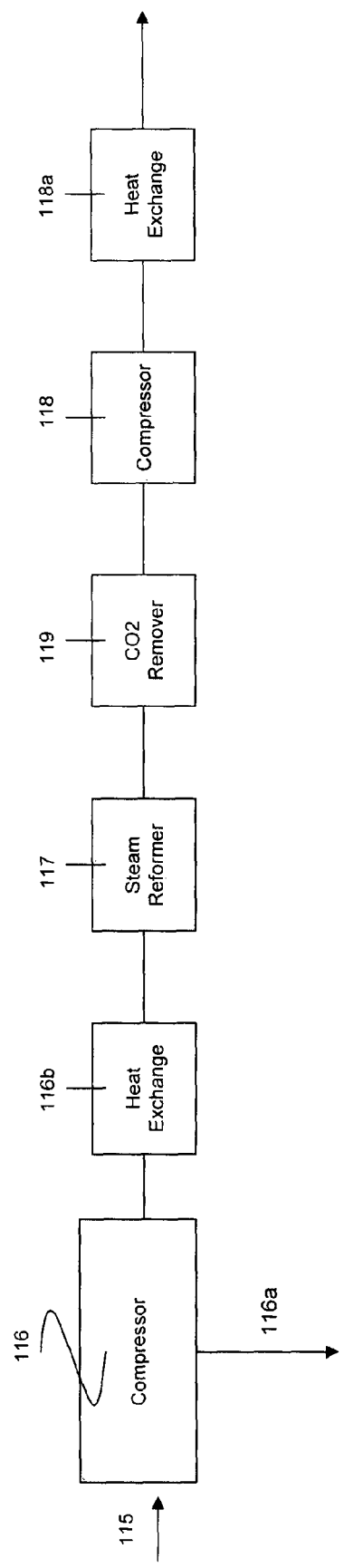
FIG. 1B is a schematic view of a preferred embodiment of the process for compressing and reforming syngas, a process of the present invention.
Figure 1C:
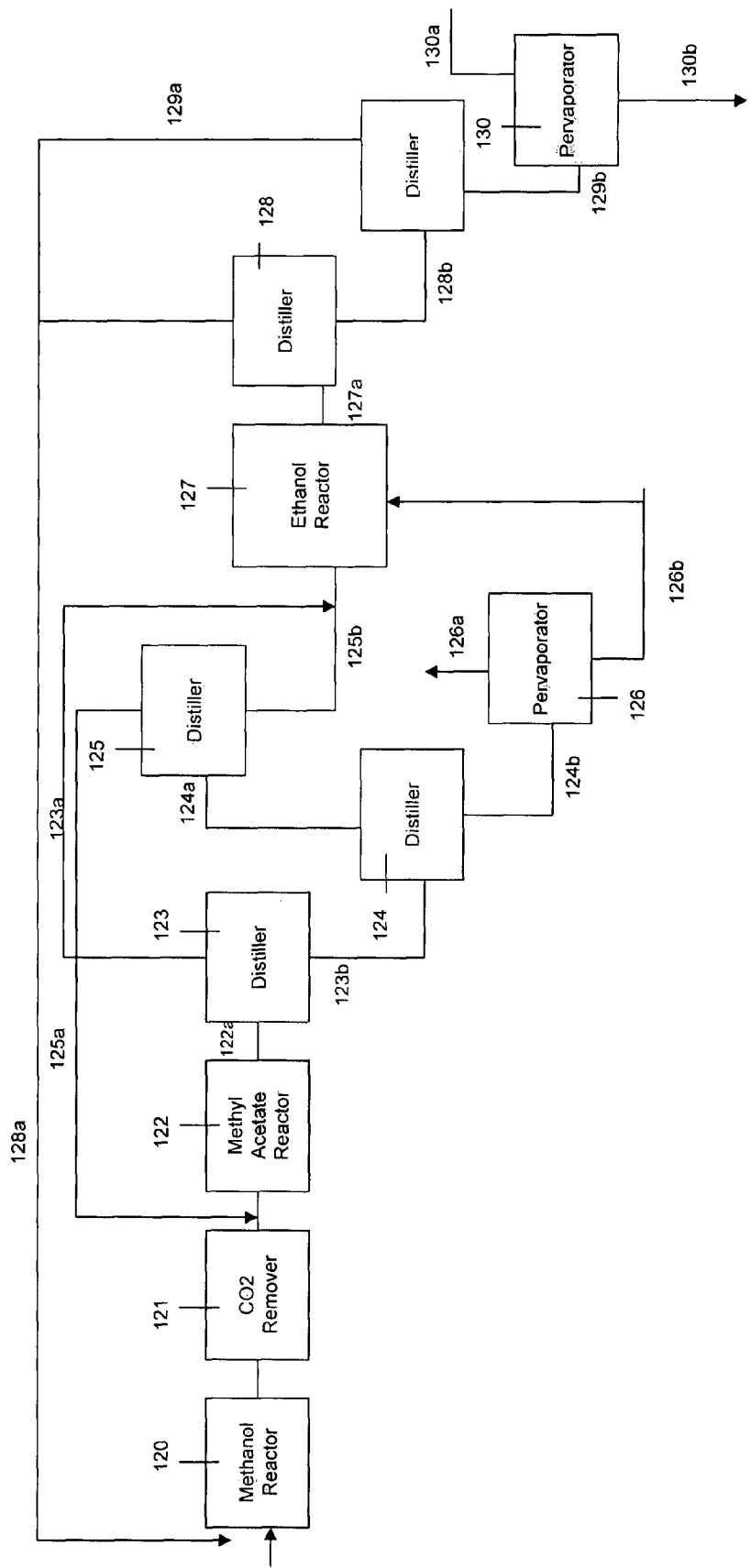
FIG. 1C is a schematic view of a preferred embodiment of the process for producing ethanol from compressed and reformed syngas, a process of the present invention.

In a preferred embodiment, as illustrated in FIGS. 1B and 1C, the synthesis gas produced by the gasification of biomass is reformed using steam, converted into methanol, then converted by carbonylation to methyl acetate (with a smaller amount of acetic acid). This methyl acetate is reacted with hydrogen in the presence of a hydrogenation catalyst to produce methanol and ethanol.

The cleaned synthesis gas stream 115 (predominately CO and $H_2$, with lesser amounts of $CO_2$ and methane) is further processed to maximize the yield of ethanol in the process. The syngas is compressed using compressor unit 116 to a pressure between 2400-3500 kPa, preferably 3200 kPa and heated to a temperature between 220 and 450 degrees Celsius (preferably 225 degrees C.) using heat exchanger 116b. This compressor is a four-stage reciprocating compressor with interstage cooling on all stages. Each stage is equipped with a water separator to remove the water condensed in each stage. Two electric motors rated at 2240 kW supply motive power for the compressors. This process produces condensed liquids 116a that are removed from the stream for recycle, further processing, or discharge.

The syngas then enters a steam reformer 117, which converts methane and other light hydrocarbons present in the synthesis gas into additional carbon monoxide and hydrogen, with the addition of steam. The steam reforming takes place in the presence of a base metal catalyst, and operates at a pressure of 3200 kPa [range: 2900-3500 kPa] and 225 C [range 220-450 C]. Steam reformation is a known technology, may be selected from a number of known commercial designs, and can be purchased from a known builder of such units such as Haldor Topsoe A/S, Lurgi AG, or ICI. Catalysts suited for this purpose comprise the well-known reforming catalysts of Group VIII in the Periodic Table, including nickel and/or cobalt, manganese-zirconium oxides. U.S. Pat. Nos. 7,090,789, and 7,074,347 are incorporated by reference. In other embodiments, the steam reformer need not be used, depending on the composition of the syngas produced by a particular biomass feedstock.

At this stage, depending on the composition of the syngas, the syngas may be subject to carbon dioxide removal, using a carbon dioxide removal system 119, such as the Praxair ethanolamine removal system. At this stage as much carbon dioxide 119a is removed as can be accomplished, by state-of-the-art equipment, from the syngas, and sent to storage, utilized elsewhere in the process, or vented to the atmosphere, depending on the circumstances. In another embodiment, this carbon dioxide removal step takes place after the second compression step 118.

Exiting from the steam reformer 117, the syngas is then further compressed to a pressure between 4700 and 5500 kPa (preferably 4900 kPa) and heated to a temperature between 220 and 300 degrees Celsius (preferably 225 degrees C.), and any condensed liquids 118a are removed for recycle, further processing, or discharge. Like the compressor 116, this compressor 118 is a four-stage reciprocating compressor with interstage cooling on all stages. Each stage is equipped with a water separator to remove the water condensed in each stage. Two electric motors rated at 2240 kW supply motive power for the compressors. A heat exchanger 118a is used to heat the gas to the operating temperature.

At this point, the compressed syngas 116a leaving the compressor 116 is at a pressure of 4900 kPa [range: 4700-5500 kPa] and 225 C [range 220-300 degrees C], the syngas is now at a temperature and pressure optimal for the first catalytic step. The synthesis gas is then fed to the first step in the chemical reaction sequence, which is conversion of the syngas to methanol 120. The conversion of synthesis gas to methanol is a well-established process, and can be achieved either through gas-phase or liquid-phase reactions. Methanol is commonly produced from synthesis gas produced by the steam reforming of natural gas and many commercial facilities are in operation today.

In this embodiment of a methanol reactor, carbon monoxide and hydrogen are combined to form methanol at a ratio of 1:2, respectively. In the preferred embodiment, a slurry reactor is used. In the slurry embodiment, methanol reactor 120 is a commercially available methanol reactor available from Air Products, which would provide an added benefit of having the commercial producer engineer and guarantee its performance. The Air Products reactor process is extremely efficient and is utilized in the largest coal-to-methanol facility in the world in Kingsport, Tenn. In the preferred embodiment, the reactor 120 is a vertical vessel with internal vertical tubes. The catalyst in the methanol reactor is composed of base metals, and operates at a pressure of 4900 kPa [range: 4700-5500 kPa] and 225 degrees C. [range 220-300 degrees C]. One embodiment comprises copper and zinc oxides on alumina, suspended in an inert mineral oil. The pressurized synthesis gas is bubbled through the vessel containing the mineral oil catalyst and escapes through the top of the vertical vessel. In the preferred embodiment, the synthesis gas entering the vessel will contain some methanol. This additional methanol is provided by recycling methanol recovered from the ethanol reactor. U.S. Pat. Nos. 3,888,896, 4,031,123, 4,639,470, 4,910,227, 4,628,066, 4,567,204, and 4,628,066 are incorporated here by reference. Because the reaction is exothermic, cooling water is provided for the generation of steam in the tubes.

Published information from Air Products discloses that a hydrogen to carbon monoxide ratio of from 0.6 to 4.0 can be used to produce methanol. The methanol reactor is capable of yields converting 20 to 90% of the carbon monoxide to methanol in the reactor, though typically falling in the 40 to 70% range.

In this embodiment of the methanol reactor, during the time the synthesis gas is resident in the methanol reactor, the required hydrogen concentration may be adjusted by adding steam to the gases entering methanol reactor and also by removing carbon dioxide. This step may be desirable because the ratio of hydrogen to carbon dioxide in the synthesis gas may not be optimal for the high yield production of ethanol. In this embodiment, the methanol catalyst will, in the presence of steam, convert carbon monoxide into hydrogen and carbon dioxide, thus increasing the hydrogen to carbon monoxide ratio. This reaction occurs under similar pressure and temperature conditions as the methanol conversion, and is known to be capable of completed in a one step fashion. U.S. Pat. No. 4,946,477 discloses this type of combined methanol/shift reaction and is incorporated by reference. U.S. Pat. No. 4,980,145 is also incorporated by reference.

In this embodiment combining methanol and shift reactions, a carbon dioxide removal unit 121 is interposed at the outlet of the methanol reactor 120 to remove carbon dioxide formed in the water gas shift. The hydrogen concentration at the outlet of the methanol reactor can be controlled by removing the carbon monoxide and controlling the amount of steam supplied, as well as by controlling the amount of methanol and hydrogen recycled to the inlet of the methanol reactor 127.

Other embodiments exist for the methanol reactor. For example, a packed solid bed of catalyst on an inert material may be used, and the syngas passed through this packed bed. The usual methanol catalysts can be used in such a method.

Alternate catalysts may be used in other embodiments. The methanol synthesis catalyst used in the process of this invention may include an oxide of at least one element selected from the group consisting of copper, silver, zinc, boron, magnesium, aluminum, vanadium, chromium, manganese, gallium, palladium, osmium and zirconium. The catalyst may be a copper based catalyst, such as copper oxide. The process may use a copper based catalyst, which also includes an oxide of at least one element selected from the group consisting of silver, zinc, boron, magnesium, aluminum, vanadium, chromium, manganese, gallium, palladium, osmium and zirconium.

The mixture of methanol, CO and hydrogen in this embodiment, which may also contain water vapour from the water gas shift reaction, passes from the methanol reactor to the methyl acetate reactor 122. The methyl acetate reactor in this embodiment is a packed bed reactor comprised of one or more vertical tubes approximately one inch wide (range one-half to 2 inches) and 20 feet long (range 15 to 30 feet). The catalyst used in the preferred embodiment of the reactor 122 is composed of iridium acetate adsorbed onto activated carbon and is packed into the vertical tubes. The reactor operates at a temperature between 200 and 300 degrees Celsius (optimally 220 degrees C.) and a pressure between 1000 and 1200 kPa (optimally 1034 kPa). Methyl iodide gas is added as a promoter to the gases before they enter the inlet of the reactor, and the reaction proceeds in the tubes to produce a mixture of predominately methyl acetate, along with hydrogen and small quantities of acetic acid and water at the outlet. The reaction is exothermic, and the reactor vessel is indirectly cooled using a heat exchange medium such as Dowtherm which runs, either in tubes through the vessel, or as a jacket around the packed tubes.

In other embodiments, a wide variety of heterogeneous catalysts may be used. These catalysts are useful in carbonylation of methanol: $RhX_3$, $RhX_3 \cdot 3H_2O$, $Rh_2(CO)_4 X_2$, [Rh(CO)$X_4$]Y, $Rh_2(CO)_8$, $Rh(NO)_3$, [Rh(CO)$_2$ $X_2$]Y, $Rh_2O_3$, $Rh(CH_3COO)_3$, [Rh($C_2H_4$)$_2$X]$_2$, Rh[($C_6H_5$)$_3$P]$_2$(CO)X, Rh metal, RhX[($C_6H_5$)$_3$P]$_2$(CH$_3$X)$_2$, Rh(SnX$_3$)[($C_6H_5$)P]$_3$. RhX(CO)[($C_6H_5$)$_3$Q]$_2$, ($R_4Z$)[Rh(CO)$_2$X]$_2$, ($R_4Z$)$_2$Rh(CO)X$_4$], RhX[($C_6H_5$)$_3$P$_{-9}$]$_3$, RhX[($C_6H_5$)$_{-3}$P]H$_2$, [($C_6H_5$)$_3$P]$_3$ Rh(CO)H and Y$_4$ Rh$_2$ X$_2$ (SnX$_3$)$_4$ wherein X is Cl, Br or I; Y is Na, Li or K; Z is N, As or P; Q is As, P or Sb; and R is a C$_1$ to C$_{12}$ alkyl or aryl group.

In further embodiments, a second co-catalyst can also be used. Such secondary catalysts may be chosen from CoCl$_2$, RuCl$_3$, PdCl$_2$, PtCl$_2$, CuCl$_2$, AgNO$_3$, AuCl$_3$, CdCl$_2$, ZnCl$_2$, OsCl$_3$, IrCl$_3$, NiCl$_2$, MnCl$_2$, ReCl$_5$, CrCl$_3$, MoCl$_3$, WCl$_6$, VCl$_3$, NbCl$_5$, TaCl$_5$, TiCl$_4$, ZrCl$_4$, HfCl$_4$, LiI, NaI, KI, RbCl, BeCl$_2$, MgCl$_2$, CaCl$_2$, SrCl$_2$, BaCl$_2$. U.S. Pat. No. 5,414,161 is incorporated by reference.

A wide variety of promoters beside methyl iodide may be used in other embodiments. These promoters include but are not limited to $CH_3$ Br, $CH_3$ Cl, $I_2$, $Br_2$, $Cl_2$, HI, HBr, HCl.

In other alternative embodiments, the reactor may be a liquid phase reactor. In one embodiment, a solid catalyst such as those listed above may be suspended in an inert liquid such as mineral oil. In such an embodiment, the gaseous reactants may be bubbled through the inert liquid.

In another embodiment of a carbonylation reaction, the catalyst is a homogeneous catalyst, composed of a complex of one or more Group VIII metals dissolved in a solution. In this embodiment, the gaseous reactants are dissolved in the solution containing the catalyst and reacted under suitable conditions. In this embodiment, the reaction solution is distilled one or more times to separate the solution containing catalyst from the products of the carbonylation.

A number of Group VIII complexes are suitable for homogeneous catalysis of carbonylation in this embodiment. These catalysts include $IrCl_3$, $Ir_3$, $IrBr_3$, [Ir(CO)$_2$ I]$_2$, [Ir(CO)$_2$Cl]$_2$, [Ir(CO)$_2$ Br]$_2$, [Ir(CO)$_2$ I$_2$]$^-$, [Ir(CO)$_2$ Br$_2$]$^-$, [Ir(CO)$_2$ I$_2$]$^-$, [Ir(CH$_3$)I$_3$(CO)$_2$]$^-$, Ir$_4$(CO)$_{12}$, IrCl$_3 \cdot 4H_2O$, IrBr$_3 \cdot 4H_2O$, Ir$_3$(CO)$_{12}$, iridium metal, Ir$_2$O$_3$, IrO$_2$, Ir(acac)(CO)$_2$, Ir(acac)$_3$, [Ir$_3$O(OAc)$_6$(H$_2$O)$_3$][OAc], and hexachloroiridic acid [H$_2$IrCl$_6$], [Rh(CO)$_2$Cl]$_2$, [Rh(CO)$_2$I]$_2$, [Rh(Cod)Cl]$_2$, rhodium (III) chloride, rhodium (III) chloride trihydrate, rhodium (III) bromide, rhodium (III) iodide, rhodium (III) acetate, rhodium dicarbonylacetylacetonate, RhCl$_3$(PPh$_3$)$_3$ and RhCl(CO)(PPh$_3$)$_2$. U.S. Pat. Nos. 5,773,642, 5,883,289, 5,877,348, 5,917,089, 5,750,007, 5,874,610, 5,883,295, 5,663,430, 5,625,094, and 7,115,774 are incorporated herein by reference, and disclose methods for homogeneous carbonylation of alcohols such as methanol to esters.

In a still further embodiment, the carbonylation reaction can be carried out in a reactive distillation vessel. The reactants in this case are cooled and fed into such a reaction vessel containing a catalyst. The reactor heats the vessel, stripping off lighter boiling products, such as methyl acetate, in order to drive the reaction toward the products.

In other embodiments, alternate catalyst promoters are used, such as halogenated alkanes other than methyl iodide, such as ethyl bromide, or ethyl iodide.

Returning to FIG. 1C, The mixture emerging from the methyl acetate reactor 120a must be separated from the promoter. The mixture emerging from the methyl acetate reactor first subject to flash distillation in a flash distiller unit 123 or other suitable separator, where the hydrogen is removed from the remainder of the mixture. The hydrogen 123a is fed directly to the ethanol reactor 127. The remainder of the mixture 123b, comprising methyl acetate, methanol, water, and acetic acid, is fed to a distillation column 124, where a mixture 124a of methyl iodide, methyl acetate, hydrogen and methanol are separated from a mixture 124b of acetic acid and water. The methyl iodide, methyl acetate, and methanol mixture 124a is sent to a distillation column 125, where methyl iodide 125a is recovered and separated as an azeotropic mixture in the vapor phase. The methyl iodide promoter 125a is then recycled to join the gases entering the methyl acetate reactor 122. The methyl acetate and methanol mixture 125b is sent to the ethanol reactor 127.

In another embodiment, the mixture emerging from the methyl acetate reactor is fed to a distillation column separating a liquid portion of water and acetic acid, and a vapor portion of methyl acetate, methyl iodide, hydrogen and methanol. The mixture of methyl acetate, methyl iodide and methanol are sent to a second distillation apparatus, separating methyl iodide in the vapor phase and recycling back to the methyl acetate reactor. The remaining methyl acetate, methanol and hydrogen are sent to the ethanol reactor 127.

In the preferred embodiment, the acetic acid and water are sent to another distillation column 126, which removes most of the water from the acetic acid 126*b*. The acetic acid 126*b* is then vaporized fed to the ethanol reactor 127. The water 126*a* is removed, for use in the process or discharged.

The ethanol reactor 127 is a packed bed reactor operating at a temperature range of 160 to 300 degrees Celsius (optimally around 260 degrees C.) and in a pressure range of 3500 to 4500 kPa (optimally 4000 kPa). The catalyst is a commercially known hydrogenation catalyst composed of chromium, nickel and copper, available from Degussa. The catalyst is loaded in a packed bed with an inert material. The vessel in this embodiment is one or more vertical tubes, approximately one half inch to two inches in inner diameter and 20 feet long (range of 15 to 30 feet). Excess hydrogen is used in the reaction, in the preferred embodiment an excess of 10:1 hydrogen to methyl acetate (this can range from no excess to 15:1 excess). The hydrogen is already present in the mixture of reactants. If there is insufficient hydrogen, an external source can be used. The reaction in the ethanol reactor is exothermic and the reactor vessel is indirectly cooled using a heat exchange medium, such as Dowtherm which runs in tubes through the vessel, or as a jacket surrounding the vessel tubes.

In other embodiments, a variety of hydrogenation catalysts can be used. The hydrogenation catalyst which may be employed in the hydrogenation reaction includes those compounds containing copper, e.g., Cu—Co—Zn, Cu—Zn—Fe, Cu—Co—Zn—Fe, Cu—Co—Zn—Fe—Ca, Cu—Co—Zn—Mo—Na and Cu—Co—Zn—Fe. The catalyst may be prepared by adding a solution of $(NH_4)_2CO_3$ dissolved in distilled water to a solution of at least one metallic compound selected from the group consisting of $Zn(OAc)_2 \cdot 2H_2O$, $Co(OAc)_3 \cdot H_2O$, $Cu(OAc)_2 \cdot H_2O$, $Fe(NO_3)_3 \cdot 9H_2O$, $(NH_4)_6Mo_7O_{24} \cdot 4H_2O$, $Ca(NO_3)_2 \cdot 4H_2O$, NaOH, $K_2PtCl_4$, $PdCl_2$, $RhCl_3$, $RuCl_3$, $NiCl_2$, $CrCl_3$, $WCl_3$, $OsCl_3$ and $AlCl_3$, drying the result mixture at a temperature of about 120.degree. C. overnight and calcining the dried material at a temperature of about 450.degree. C. and for a period of about 16 hours. The metallic compound may be employed in an amount ranging from 0.01 to 95 wt %, more preferably from 0.1 to 80 wt % and most preferably from 1 to 50 wt %. Many other catalysts for this type of ester to acid reaction are available and characterized. U.S. Pat. Nos. 5,414,161, 5,233,099, 5,233,100, and 6,002,054 are incorporated by reference.

In returning to FIG. 1C, the effluent stream 127*a* from the hydrogenation reactor consists of methanol, ethanol, hydrogen and water. The hydrogen 128*a* is separated from this mixture in a distillation column 128 by flash distillation or other distillation, and the hydrogen 128*a* is recycled back to the inlet of the methanol reactor 120. The remaining mixture 128*b* of ethanol, methanol and water is distilled in a distilling apparatus 129 and the methanol 129*a* in the vapour fraction is recycled to the inlet of the methanol reactor.

The remaining ethanol fraction 129*b*, with less than 20% water, is then sent to a pervaporation unit 130, such as those designed by Sulzer, to separate the water 130*b* and produce specification-grade ethanol. The anhydrous alcohol 130*a* from the ethanol pervaporation unit is then directed to the storage tanks. Two storage tanks are provided for ethanol storage with a total capacity of 4,700,000 Litres (1.2 mM US gallons) (approximately 21 days operation). Gasoline for denaturing is injected prior to storage. Gasoline denaturant is mixed with the pure ethanol on 5.263% volume basis. The gasoline storage tank has a capacity of 235,000 Litres (62,500 US gallons), which is sufficient for approximately 16 days of operation.

Figure 6:
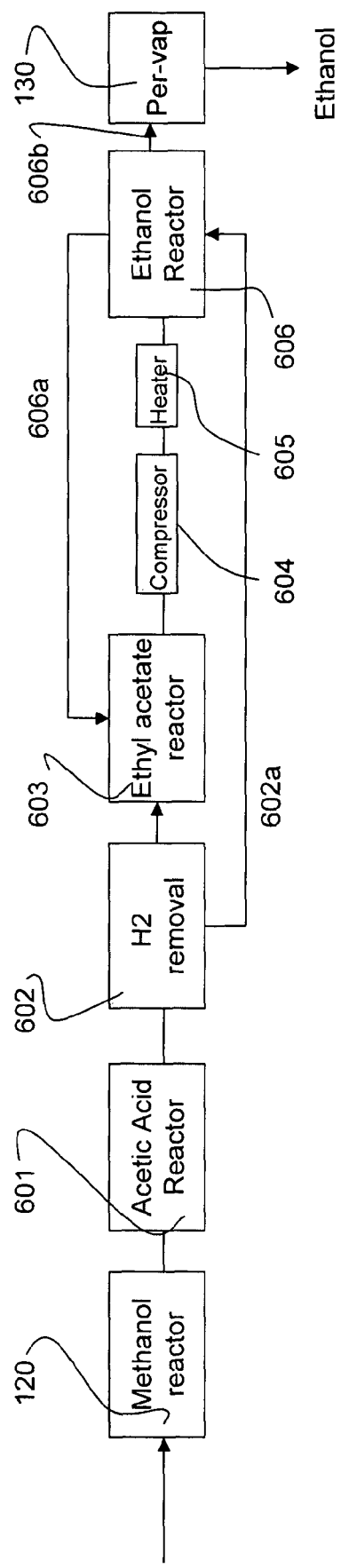
FIG. 6 is a schematic view of a preferred embodiment for producing ethanol from syngas, a process of the present invention.

In another embodiment of the invention, a route to ethanol via a four reactor carbonylation may be used, as illustrated in FIG. 6. In this embodiment, the syngas stream 115 is converted in the methanol reactor 120, as previously outlined. These gases are transferred to a liquid phase reactor 601, where they are contacted with a catalyst, for example, iridium on carbon. Rhodium may also be effective for this reaction, as well as other Group VIII metals on solid supports. Some known effective catalysts that may be used in this carbonylation are $Ir_4(CO)_{12}$, $IrCl_3$, dicarbonyldiiodide rhodium, $RhCl_3$, $RhI_3$, $RhI_2(CO)_2$. In this embodiment, the reactants are reacted under pressure between 140 and 160 psi, and at a temperature between 215 and 250 degrees Celsius, in a solution of a promoter, such as an alkyl halide. Methyl iodide may be such a promoter, though others, such as $CH_3Br$, $CH_3Cl$, $I_2$, $Br_2$, $Cl_2$, HI, HBr, HCl.

The products of this reaction are acetic acid, hydrogen, and water. The hydrogen must be removed from solution by distilling in a distiller 602. The hydrogen 602*a* is sent to the ethanol reactor 127. In the next step, the acetic acid and water is sent to a reactor 603 where ethanol is added in the presence of an oxidizing catalyst such as sulfur oxide. This reaction takes place in the liquid phase, at around atmospheric pressure (15 to 25 psi) and a Temperature between 90 and 110 degrees Celsius (preferably 100 degrees Celsius). The last step can occur after the products, ethyl acetate and water are raised in temperature in heater 604 to between 250 and 270 degrees Celsius, and compressed in compressor 605 to a pressure between 580 and 610 psi, which are the conditions of the ethanol reactor 606. The hydrogen 602*a* is added to the reactants ethyl acetate and water to produce ethanol and water. Similar hydrogenation catalysts as those used for the methyl acetate process may be used here, such as Cu—Cr—Ni in a packed bed catalyst.

The resulting stream of ethanol and water is split into two streams, where 606*a* is transferred to the ethyl acetate reactor 603, and the rest 606*b* is pervaporated in Sulzer pervaporation unit 130 to separate remaining water from the ethanol. In this manner, ethanol is formed from syngas.

Figure 8:
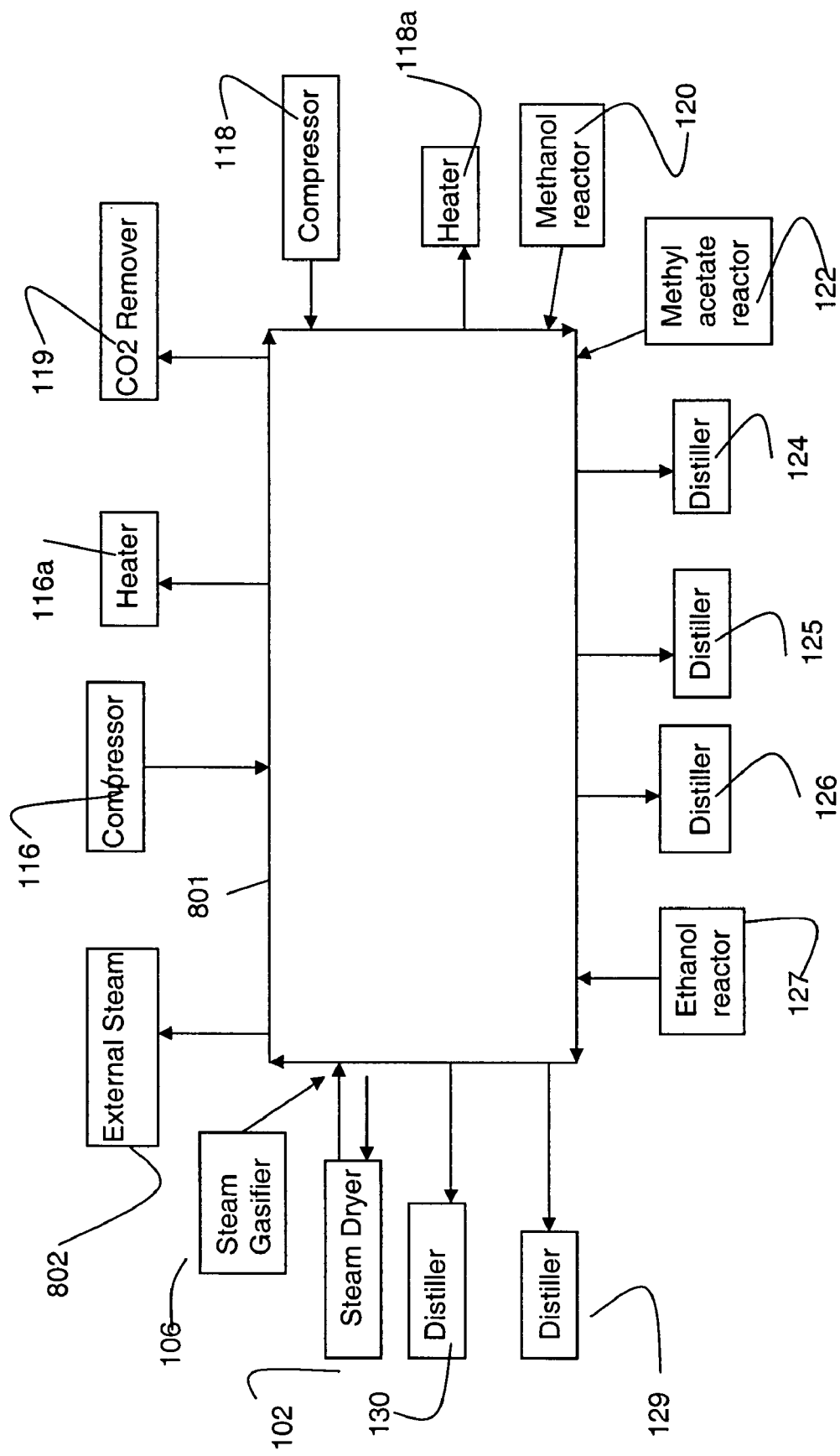
FIG. 8 is a schematic view showing the use of liquid heat transfer medium to distribute heat flows throughout the process.

It has been previously noted that the ethanol reactor 127, the methyl acetate reactor 122, and the methanol reactor 120 of FIG. 1C are exothermic, and that the methyl acetate and ethanol reactors employ a liquid transfer medium such as Dowtherm to cool the reactions. A liquid heat exchange medium, can thus be used to transfer this heat to other processes that require heat. Thus, it is possible to devise a loop of liquid heat exchange medium that can transfer heat around a plant. Such a scheme is illustrated in FIG. 8. This illustration shows a flow of liquid heat exchange medium 801 around the plant. The various process equipment along this loop, such as distillers or reactors are engineered so as to have heat exchange surfaces capable of contacting the liquid reaction medium and transferring heat to or from the medium. In one step, the liquid medium applies heat to the dryer 102 of FIG. 1A. The dryer, by cooling its exhaust steam can also provide heat to the liquid medium by contacting the exhaust gases with the liquid medium. The dryer, at the same time, requires heat to produce the steam used to dry biomass, and can use liquid medium for that purpose.

In this embodiment, the loop, which can be created by lines carrying the liquid medium between the components of the plant, can be directed to the interstage compression units 116 and 118 of FIG. 1B, which generate heat that can be transferred to the medium. Along the same route, the medium 801 transfers heat by contacting heat exchangers 116*a* and 118*a* of FIG. 1B. The medium can further transfer heat to the $CO_2$ removal system 119.

In a further elaboration, the liquid transfer medium can receive heat by coming in thermal contact with flue gases emerging from the steam gasifier 106, methanol reactor 120, the methyl acetate reactor 122, and the ethanol reactor 127 of FIG. 1C. In similar manner, the medium can transfer heat to the distillation apparatuses 124, 125, 126, 129 and 130 of FIG. 1C.

In other embodiments, the liquid medium can be used to heat steam in an exchanger 802 for use in outside processes. This example is merely illustrative, and does not exhaust the possibility for using liquid heat transfer medium. The distillation process employ a chilling step to make the reaction composition liquid, and this chilling step can be used to transfer heat to the medium. The use of such medium will of course be highly dependent on the specific plant, and must be calibrated to best balance the flows of heat through the system.

In this manner, along with the heat recovery from flue gases and syngas, it can be seen that the biomass to ethanol process proceeds making the most use of heat available, and thus minimizes the amount of external fuels to run the process.

Several utility systems are required throughout the plant. These include High Pressure Steam, Medium Pressure Steam, Low Pressure Steam, Cooling Water, Instrument Air, Control System, Electrical, Fuel Gas and Auxiliary Flare, Product Water Conditioning, and Boiler Feed Water Conditioning. Cooling water is required in the ethanol distillation system. Dowtherm is used to supply heat for the distillation columns as well as removing heat from the methanol, methyl acetate and ethanol reactors. Two 100% screw air compressors operating at 760 kPag provide instrument air. The instrument air dryers, based on Silica Gel dehydration technology, will supply instrument air at a minus 50° C. dew point (@ 700 kPag). A 60-minute instrument air supply will be accumulated in the Dry Air Receiver between normal and minimum pressures. Process control will be accomplished by Distributed Control System (DCS) based instruments (Transmitters/Transducers) located throughout the plant facility mounted on processing equipment. Alarming and shutdown control will be accomplished by field signals sent to and from a DCS in the control room and will be tracked by a Sequence Event Data Recorder for subsequent analysis. Flow metering devices will send information to the PLC for local display of current flow and totalized flows. Inputs and outputs from process instrumentation and equipment where shown on the P&IDs are monitored and controlled by the PLC located in the Facility Control Room. All process points from field control cabinets that have I/O suitable for the area. All field wiring will be intrinsically safe by using current limiting devices in the local control cabinet. Analog and digital signals to and from the field devices will be by intrinsically safe I/Os. The control system will use a 24V DC control loop for field instruments. Battery backup of the control system will be provided by a true on-line (load is always connected to the inverter) interruptible power system capable of maintaining system operation for one hour. Process quality will be by installed analyzers that will provide online indication of required process data. Data will be archived for analysis at a later date. The entire control system and process variables will also be capable of remote monitoring by the operator to ensure mechanical and process efficiency is maintained.

It will be appreciated that the above description related to the invention by way of example only. Many variations on the invention will be obvious to those skilled in the art and such obvious variations are within the scope of the invention as described herein whether or not expressly described.

What is claimed is:

1. A method of producing ethanol from syngas comprising:
providing a syngas comprising carbon monoxide, hydrogen and carbon dioxide;
removing a portion of carbon dioxide from the syngas to produce a reduced carbon dioxide syngas;
converting the reduced carbon dioxide syngas in the presence of a catalyst to produce a mixture comprising methanol and carbon monoxide and hydrogen;
producing a mixture comprising methyl acetate, hydrogen, methanol, acetic acid, and water from the mixture comprising methanol and carbon monoxide and hydrogen, by reacting the methanol and carbon monoxide in the presence of a promoter and a metal catalyst comprising a metal selected from the group consisting of iridium, rhodium, iron, cobalt, nickel, ruthenium, palladium, osmium, and platinum, and the promoter;
distilling the hydrogen from the mixture of methyl acetate, hydrogen, methanol, acetic acid, and water by flash distillation to produce a mixture comprising methyl acetate, methanol, acetic acid and water, wherein the flash distilled hydrogen is subsequently used in the production of ethanol;
separating the mixture comprising methyl acetate, methanol, acetic acid and water to produce a mixture comprising methyl acetate and methanol and at least one fraction selected from the group consisting of a promoter fraction, an acetic acid fraction, and a water fraction; and
producing a mixture comprising ethanol by reacting the methyl acetate and methanol mixture with hydrogen in the presence of a hydrogenation catalyst.

2. A method of producing ethanol as claimed in claim 1, wherein the catalyst comprising a metal is an iridium catalyst.

3. A method of producing ethanol as claimed in claim 1, wherein the catalyst comprising a metal is iridium acetate.

4. A method of producing ethanol as claimed in claim 1, wherein the promoter is an alkyl halide.

5. A method of producing ethanol as claimed in claim 4, wherein the promoter is methyl iodide.

6. A method of producing ethanol as claimed in claim 1, further comprising:
providing a syngas comprising carbon monoxide, hydrogen and carbon dioxide;
compressing the syngas to produce compressed syngas;
heating the compressed syngas to produce heated compressed syngas;
steam reforming the heated compressed syngas to produce reformed syngas;
removing carbon dioxide from the syngas to produce a reformed reduced carbon dioxide syngas;
recompressing the reformed reduced carbon dioxide syngas to produce compressed reformed reduced carbon dioxide syngas; and
converting the compressed reformed reduced carbon dioxide syngas into a mixture comprising methanol, carbon monoxide, and hydrogen.

7. A method of producing ethanol as claimed in claim 6, wherein steam reforming the compressed syngas is performed at a pressure from 2400 to 3500 kPa.

8. A method of producing ethanol as claimed in claim 6, wherein converting the compressed reformed reduced carbon dioxide syngas into the mixture comprising methanol further comprises:
bubbling the compressed reformed reduced carbon dioxide syngas through a slurry to produce methanol, wherein said slurry contains a metallic catalyst suspended in an inert liquid.

9. A method of producing ethanol as claimed in claim 8, wherein converting the compressed reformed reduced carbon dioxide syngas into the mixture comprising methanol further comprises:
adding steam to the compressed reformed reduced carbon dioxide syngas to produce hydrogen that is added to the compressed reformed syngas.

10. A method of producing ethanol as claimed in claim 1, further comprising recycling the promoter fraction to the mixture comprising methanol, carbon monoxide and hydrogen that is reacted to produce the mixture comprising methyl acetate, hydrogen, methanol, acetic acid and water.

11. A method of producing ethanol as claimed in claim 1, further comprising recycling the acetic acid fraction to the mixture of methyl acetate and methanol that is used to produce a mixture comprising ethanol by reacting the methyl acetate methanol and acetic acid mixture with hydrogen in the presence of a hydrogenation catalyst.

12. A method of producing ethanol as claimed in claim 1, wherein a packed bed reactor is used for producing the mixture comprising ethanol.

13. A method of producing ethanol as claimed in claim 12 wherein said packed bed reactor contains a catalyst comprised of copper, nickel, chromium, or a combination thereof.

14. A method of producing ethanol as claimed in claim 1, wherein producing the mixture comprising ethanol is carried out in the gas phase at a temperature from 160 to 300 degrees Celsius and at pressure from 3500 to 4500 kPa.

15. A method of producing ethanol as claimed in claim 1, wherein producing the mixture comprising ethanol is carried out with a ratio of hydrogen to methyl acetate of from 2:1 to 15:1.

16. A method of producing ethanol as claimed in claim 1, wherein producing the mixture comprising methyl acetate, hydrogen, methanol, acetic acid and water is carried out in a packed bed carbonylation reactor.

17. A method of producing ethanol as claimed in claim 16, wherein said packed bed carbonylation reactor is packed with an activated carbon material on which is adsorbed the metal catalyst.

18. A method of producing ethanol as claimed in claim 1 wherein producing the mixture comprising methyl acetate, hydrogen, methanol, acetic acid and water is performed in the gas phase at a pressure from 1000 to 1500 kPa, and at a temperature from 200 to 300 degrees Celsius.

19. A method of producing ethanol as claimed in claim 1, wherein said separating comprises:
distilling the mixture comprising methyl acetate, methanol, acetic acid and water to separate and recycle unreacted components and promoter.

20. A method according to claim 19, wherein the promoter is methyl acetate, which following flash distillation of the hydrogen results in a mixture comprising acetic acid, methyl acetate, methyl iodide, methanol and water.

21. A method according to claim 20 further comprising distilling the mixture comprising acetic acid, methyl acetate, methyl iodide, methanol and water to produce a mixture comprising methyl acetate and methyl iodide, and a mixture comprising acetic acid and water.

22. A method according to claim 21, further comprising distilling the mixture of methyl acetate and methyl iodide to produce a methyl acetate fraction and a methyl iodide fraction; and
removing water from the mixture comprising acetic acid and water to produce an acetic acid fraction.

23. A method of producing ethanol as claimed in claim 1, further comprising
separating the mixture comprising ethanol to produce an ethanol fraction, a methanol fraction, and a second hydrogen fraction;
recycling the methanol fraction to the mixture comprising methanol and carbon monoxide and hydrogen that is used to produce the mixture comprising methyl acetate, hydrogen, methanol, acetic acid, and water, or to the mixture of methyl acetate and methanol that is used to produce a mixture comprising ethanol; and
recycling the second hydrogen fraction to the mixture comprising methyl acetate and methanol that is used to produce a mixture comprising ethanol.

24. A method of producing ethanol as claimed in claim 1, wherein providing syngas further comprises:
gasifying biomass in a steam gasifier having a fluidized bed to produce a syngas stream.

25. A method of producing ethanol as claimed in claim 24, wherein providing syngas further comprises cooling the syngas in a syngas heat recovery steam generator to generate steam.

26. A method of producing ethanol as claimed in claim 24, wherein gasifying biomass in a steam gasifier further comprises:
producing hot flue gases by burning a fuel;
transferring the hot flue gases to a series of tubes embedded in the fluidized bed of the steam gasifier to heat the fluidized bed.

27. A method of producing ethanol as claimed in claim 26, wherein said fuel is low-BTU synthesis gas produced by gasifying biomass in an air-blown gasifier.

28. A method of producing ethanol as claimed in claim 26, wherein gasifying biomass in a steam gasifier further comprises:
venting the hot flue gases to a flue gas heat recovery steam generator;
converting steam from the syngas heat recovery steam generator to steam in the flue gas heat recovery steam generator; and
transferring said steam to gasifying biomass in a steam gasifier or drying biomass in a steam dryer.

29. A method of producing ethanol according to claim 1, further comprising:
converting the syngas to methanol by bubbling syngas through an inert liquid at a pressure from 4700 to 5500 kPa, and a temperature from 220 to 300 degrees Celsius;
producing the mixture of methyl acetate, hydrogen, methanol, acetic acid and water in a packed bed reactor in the presence of a promoter, where the metal catalyst is iridium acetate adsorbed onto activated carbon, and where such reaction is carried out at a pressure from 900 to 1500 kPa, and at a temperature from 200 to 300 degrees Celsius;
producing the mixture comprising ethanol in a packed bed reactor, where the hydrogenation catalyst is comprised of copper, nickel and chromium adsorbed onto an inert material, wherein producing the mixture comprising ethanol is carried out at a temperature from 160 to 300 degrees Celsius, and at pressure from 3500 to 4500 kPa;

separating the mixture comprising methyl acetate, methanol, acetic acid and water to produce an acetic acid fraction; and adding the acetic acid fraction to the reactor to produce ethanol;

wherein providing syngas further comprises;

drying biomass in a steam dryer to a moisture content from 1% to 30%;

gasifying the biomass in a steam gasifier to produce syngas, wherein said gasifier is a box-shaped vessel having vertical walls and a ceiling; a fluidized bed comprising silica sand, dolomite or olivine, or a combination thereof; a bottom composed of a distributor plate having an interior surface and a plurality of through-holes in which are mounted cylinders having caps, wherein said capped cylinders are hollowed so as to have a channel extending from a plenum underneath the distributor plate that carries steam and wherein said channel extends and narrows to one or more outlet holes drilled in said caps, the outlet holes being transverse to a longitudinal axis of said cylinders, whereby steam is injected from the plenum through the through-holes into the bed so as to evenly fluidize the bed through the outlet holes in a direction parallel to a plane defined by the interior surface of the distributor plate; and wherein said vessel has a plurality of tubes embedded in the bed that transmit hot flue gases so as to heat the bed, and wherein said tubes are parallel to the plane of the distributor plate and are arranged in sets wherein the tubes in said sets are parallel to one another and have a triangular orientation with one another, and wherein said gasification is carried out at a temperature from 750 to 900 degrees Celsius and at a pressure from 100 to 175 kPa; and wherein said hot flue gases are produced by gasifying biomass in an air blown gasifier to produce low BTU syngas and combusting said low BTU syngas.

30. A method for producing ethanol from biomass according to claim 24, wherein converting the syngas and producing a mixture comprising ethanol further comprises using only hydrogen produced in the course of carrying out the method.

31. A method for producing ethanol from biomass according to claim 24, wherein converting the syngas and producing a mixture comprising ethanol further comprises using hydrogen from an external source.

32. A method for producing ethanol from syngas according to claim 1, further comprising:
converting the acetic acid fraction to methyl acetate;
producing a mixture comprising ethanol by reacting the methyl acetate produced from the acetic acid fraction with hydrogen in the presence of a hydrogenation catalyst.

33. A method of producing ethanol from syngas comprising:
providing syngas;
converting the syngas in the presence of a catalyst to produce a mixture comprising methanol and carbon monoxide;
producing a mixture comprising methyl acetate, hydrogen, methanol, acetic acid, and water, by reacting the methanol and carbon monoxide in the presence of a promoter and a metal catalyst comprising a metal selected from the group consisting of iridium, rhodium, iron, cobalt, nickel, ruthenium, palladium, osmium, and platinum, and the promoter;
separating the mixture comprising methyl acetate, hydrogen, methanol, acetic acid and water to produce a mixture of methyl acetate and methanol and a fraction selected from the group consisting of a hydrogen fraction, a promoter fraction, an acetic acid fraction, and a water fraction; and
producing a mixture comprising ethanol by reacting the methyl acetate and methanol mixture with hydrogen in the presence of a hydrogenation catalyst.

34. A method of producing ethanol according to claim 1, further comprising:
drying biomass in a steam dryer to a moisture content from 1% to 30%;
gasifying the biomass in a steam gasifier to produce syngas, wherein said gasifier is a cylindrical-shaped vessel having vertical walls and a ceiling; a fluidized bed comprising silica sand, dolomite or olivine, or a combination thereof; a bottom composed of a distributor plate having an interior surface and a plurality of through-holes in which are mounted cylinders having caps, wherein said capped cylinders are hollowed so as to have a channel extending from a plenum underneath the distributor plate that carries steam and wherein said channel extends and narrows to one or more outlet holes drilled in said caps, the outlet holes being transverse to a longitudinal axis of said cylinders, whereby steam is injected from the plenum through the through-holes into the bed so as to evenly fluidize the bed through the outlet holes in a direction parallel to a plane defined by the interior surface of the distributor plate; and wherein said vessel has a plurality of tubes embedded in the bed that transmit hot flue gases so as to heat the bed, and wherein said tubes are perpendicular to the plane of the distributor plate, and wherein said gasification is carried out at a temperature from 750 to 900 degrees Celsius and at a pressure from 100 to 175 kPa; and wherein said hot flue gases are produced by gasifying biomass in an air blown gasifier to produce low BTU syngas and combusting said low BTU syngas;
converting the syngas to methanol by bubbling syngas through an inert liquid at a pressure from 4700 to 5500 kPa, and a temperature from 220 to 300 degrees Celsius;
producing the mixture of methyl acetate, hydrogen, methanol, acetic acid and water in a packed bed reactor in the presence of a promoter, where the metal catalyst is iridium acetate adsorbed onto activated carbon, and where such reaction is carried out at a pressure from 900 to 1500 kPa, and at a temperature from 200 to 300 degrees Celsius;
producing the mixture comprising ethanol in a packed bed reactor, where the hydrogenation catalyst is comprised of copper, nickel and chromium adsorbed onto an inert material, wherein producing the mixture comprising ethanol is carried out at a temperature from 160 to 300 degrees Celsius, and at pressure from 3500 to 4500 kPa.

\* \* \* \* \*

UNITED STATES PATENT AND TRADEMARK OFFICE
CERTIFICATE OF CORRECTION

PATENT NO. : 8,088,832 B2
APPLICATION NO. : 11/784508
DATED : January 3, 2012
INVENTOR(S) : Melnichuk et al.

It is certified that error appears in the above-identified patent and that said Letters Patent is hereby corrected as shown below:

In column 17, line 25
Replace "acetate methanol"
With "acetate, methanol"

Signed and Sealed this
Twenty-second Day of May, 2012

David J. Kappos
*Director of the United States Patent and Trademark Office*